United States Patent [19]

Shoupe et al.

[11] Patent Number: 5,019,573
[45] Date of Patent: May 28, 1991

[54] SUBSTITUTED DIBENZOFURANS AND METHODS OF USING SAME

[75] Inventors: T. Scott Shoupe, Southbury, Conn.; David C. Baker, Tuscaloosa, Ala.; Stephen M. Coutts, Rancho Santa Fe, Calif.; Elli S. Hand, Tuscaloosa, Ala.

[73] Assignee: Euroceltique, S.A., Luxembourg, Luxembourg

[21] Appl. No.: 409,630

[22] Filed: Sep. 19, 1989

[51] Int. Cl.$^5$ ................ A61K 31/535; A61K 31/34; C07D 405/02; C07D 307/91

[52] U.S. Cl. ................ 514/232.8; 514/422; 514/468; 544/153; 548/525; 549/460; 549/461

[58] Field of Search ............ 549/460, 461; 548/525; 544/153; 514/232.8, 422, 468

[56] References Cited

U.S. PATENT DOCUMENTS 3,867,409  2/1975  Albrecht et al. ............ 544/153

Primary Examiner—Mary C. Lee
Assistant Examiner—Joseph K. McKane
Attorney, Agent, or Firm—Steinberg & Raskin

[57] ABSTRACT

Novel substituted dibenzofuran compounds are disclosed. The compounds exhibit activity in antagonizing the effects of leukotriene B$_4$ (LTB$_4$). Pharmaceutical compositions containing the novel compounds and methods of treatment employing the same are also described.

23 Claims, No Drawings

SUBSTITUTED DIBENZOFURANS AND METHODS OF USING SAME

BACKGROUND OF THE INVENTION

1. Field of the Invention

The invention relates to 2,8-disubstituted dibenzofurans, compositions containing the same and methods of using the same to antagonize the effects of leukotriene $B_4$.

2. Description of the Prior Art

Leukotriene $B_4$ ($LTB_4$) is a product of the metabolism of arachidonic acid via the lipoxygenase pathway. It is produced by a number of inflammatory cell types including neutrophils, macrophages, mast cells and epithelial cells. The structure of $LTB_4$ is as follows:

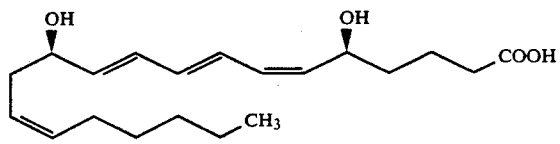

At the cellular level, release of $LTB_4$ causes the aggregation and movement (chemokinesis and chemotaxis) of leukocytes, in particular neutrophils. Other biological actions of $LTB_4$ on leukocyte function include release of lysozymal enzymes, expression of surface C3b receptors and enhancement of intraleukocyte cGMP levels. Further, it has been suggested that $LTB_4$ may regulate lymphocytic elements of the immune response in vitro. Evidence for this is demonstrated by the respective inhibitory and stimulatory effects of $LTB_4$ on the proliferation of helper-inducer and suppressor-cytotoxic T lymphocytes as well as by the modulation of monokine and lymphokine production.

The actions of $LTB_4$ are mediated through the interaction of this molecule with specific receptors on the membranes of affected cells.

Systemically, $LTB_4$ causes neutropenic effects when administered intravenously. At the cellular level, neutrophil accumulation is observed when $LTB_4$ is infused intraocularly; neutrophil accumulation accompanied by plasma exudation is seen when injected intradermally in rabbits and man.

Due to its activity as a potent chemoattractant for leukocytes, $LTB_4$ has been implicated in the pathogenesis of various inflammatory conditions including psoriasis, arthritis, gout, cystic fibrosis, inflammatory bowel disease and pulmonary microembolization syndromes. Indeed, it is possible to speculate upon the importance of $LTB_4$ as a mediator in any condition characterized by an infiltration of white blood cells.

Antagonists of the interaction of $LTB_4$ with its receptor would be used in the treatment of any of the previously mentioned inflammatory conditions as well as immune system disorders.

SUMMARY OF THE INVENTION

The present invention relates to a new class of compounds based on 2,8-disubstituted dibenzofurans having the following generic structure:

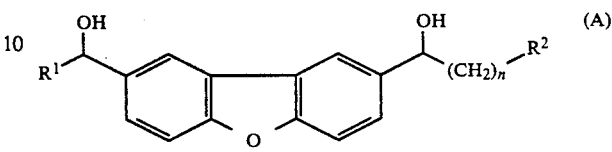

The novel compounds have been found to inhibit certain types of cellular responses presumed to be mediated via specific interactions of $LTB_4$ with cellular receptors.

Pharmaceutical compositions containing compounds of formula A, as well as methods of treatment utilizing such compositions are also included within the present invention.

DETAILED DESCRIPTION OF THE INVENTION

The novel compounds of the present invention are 2,8-substituted dibenzofuran diols, as reflected by formula A.

Referring to formula A: n is an integer preferably from 1 to 5; $R^1$ may be alkyl (straight-chain, branched or cyclic); phenyl; substituted phenyl (such as o, p, or m F, Cl, Br, I, $-CF_3$, $-OCH_3$, alkyl, $-CN$, $-NH_2$, $-CONH_2$ or $NO_2$, and di- and trisubstituted phenyls thereof); $Ph(CH_2)_n$ where $n=1-5$ or more in which the phenyl ring may also bear substituents; heteroaromatic; or heterocycloalkyl.

$R^2$ may be an ester moiety ($CO_2R^3$ where $R^3$ is alkyl, aryl or aralkyl); an alkanoate salt (e.g., $CO_2Na$ or $CO_2K$); an amide moiety ($C(O)NR^4R^5$ where $R^4$ is H, alkyl, aryl (substituted or unsubstituted) and $R^5=R^4$ or is one of the other $R^4$ substituents, or $R^4$ and $R^5$ constitute a ring, such as tetrazole, $-(CH_2)_5-$ or $(-CH_2CH_2)_2X$ where X is O, S, $NR^6$ ($R^6=H$, alkyl, aryl, or substituted aryl)); ether (OR); thioether (SR), sulfoxide (SOR); sulfone ($SO_2R$); sulfinic acid ($SO_2H$); sulfonic acid ($SO_3H$); or half ester of sulfur acids ($OSO_2H$, $OSO_3H$, etc.), or sulfonamides derived therefrom.

Shown below are four synthetic schemes for preparing representative compounds of the present invention. In all of these compounds, $R^1$ is benzyl ($CH_2C_6H_5$). $R^2$ and n are as indicated in Table I for the representative compounds, identified by their numerical designations in the synthetic schemes I–IV.

TABLE I

Summary of Compounds A ($R^1 = CH_2C_6H_5$).

| n | H | $CO_2H$ | $CO_2Na$ | $C(O)N(CH_3)_2$ | C(O)N⟨⟩OH | C(O)N⟨⟩O |
|---|---|---|---|---|---|---|
| 1 | 6 | 11 | | 12 | | |
| 2 | | | 26 | 22 | 23 | |
| 3 | | 45 | 40 | 41 | 42 | 25 | 43 |
| 4 | | | | | 51 | | |

Compounds shown in Schemes I–IV whose numbers are not included in Table I are intermediates useful in producing the novel substituted dibenzofurans.
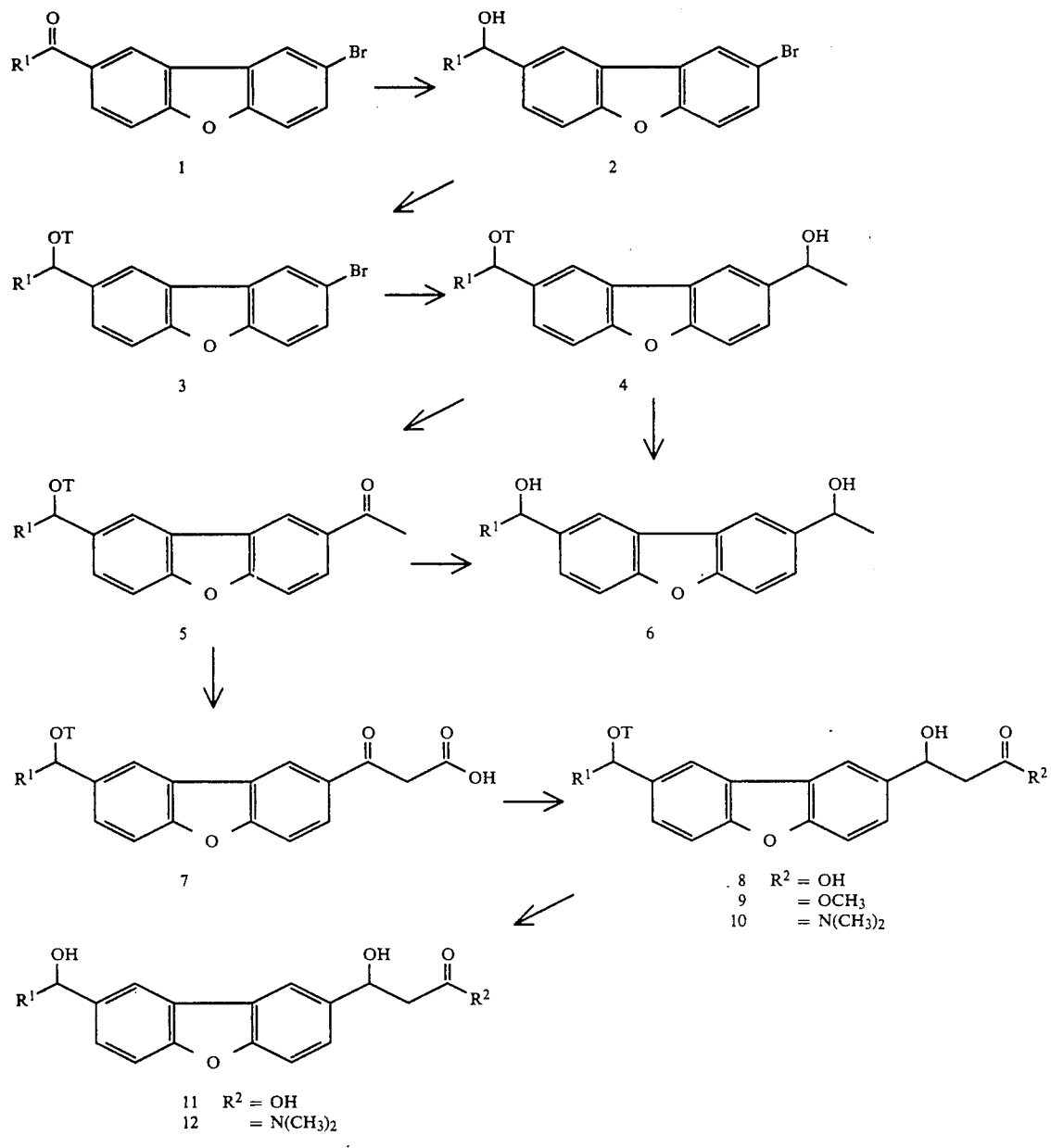
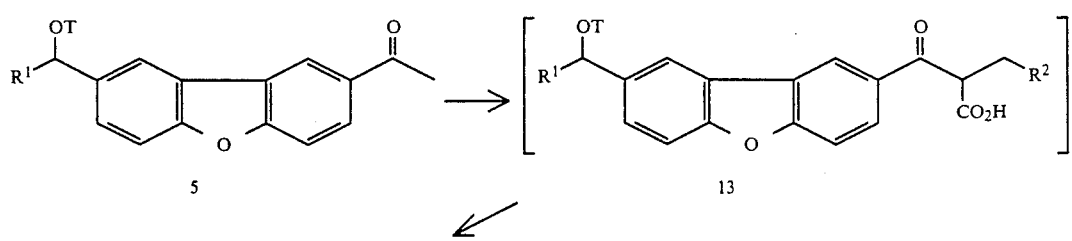

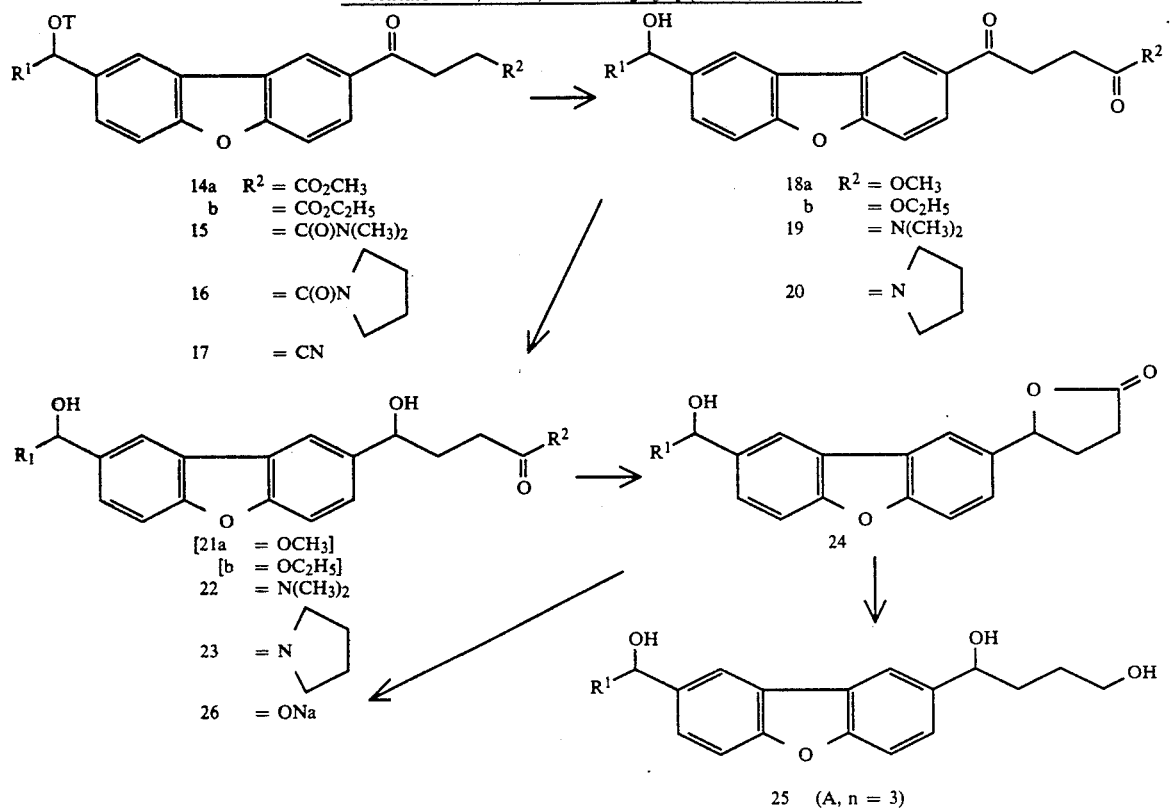

Scheme II: A, n = 2, R¹ = CH₂C₆H₅ (and 25, A, n = 3)

| | |
|---|---|
| 14a R² = CO₂CH₃ | 18a R² = OCH₃ |
| b = CO₂C₂H₅ | b = OC₂H₅ |
| 15 = C(O)N(CH₃)₂ | 19 = N(CH₃)₂ |
| 16 = C(O)N⟨pyrrolidine⟩ | 20 = N⟨pyrrolidine⟩ |
| 17 = CN | |

[21a = OCH₃]
[b = OC₂H₅]
22 = N(CH₃)₂
23 = N⟨pyrrolidine⟩
26 = ONa

T = Si(CH₃)₂C(CH₃)₃

25 (A, n = 3)

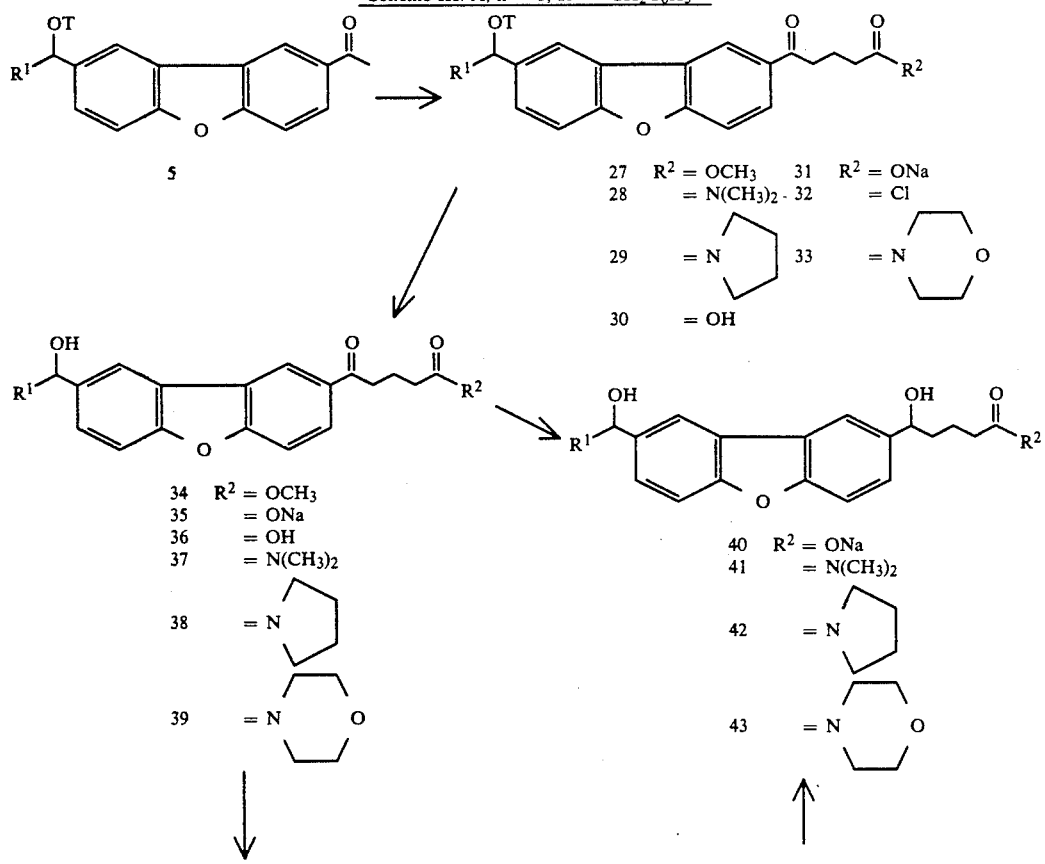

Scheme III: A, n = 3, R¹ = CH₂C₆H₅

| | |
|---|---|
| 27 R² = OCH₃ | 31 R² = ONa |
| 28 = N(CH₃)₂ | 32 = Cl |
| 29 = N⟨pyrrolidine⟩ | 33 = N⟨morpholine⟩ |
| 30 = OH | |

| | |
|---|---|
| 34 R² = OCH₃ | 40 R² = ONa |
| 35 = ONa | 41 = N(CH₃)₂ |
| 36 = OH | 42 = N⟨pyrrolidine⟩ |
| 37 = N(CH₃)₂ | 43 = N⟨morpholine⟩ |
| 38 = N⟨pyrrolidine⟩ | |
| 39 = N⟨morpholine⟩ | |

-continued

Scheme III: A, n = 3, R¹ = CH₂C₆H₅

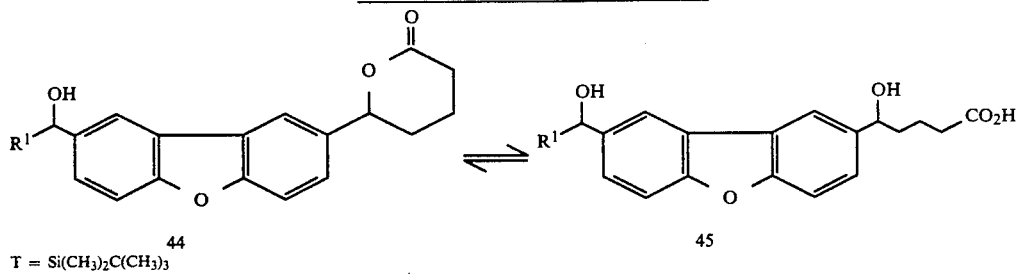

T = Si(CH₃)₂C(CH₃)₃

Scheme IV: A, n = 4, R¹ = CH₂C₆H₅

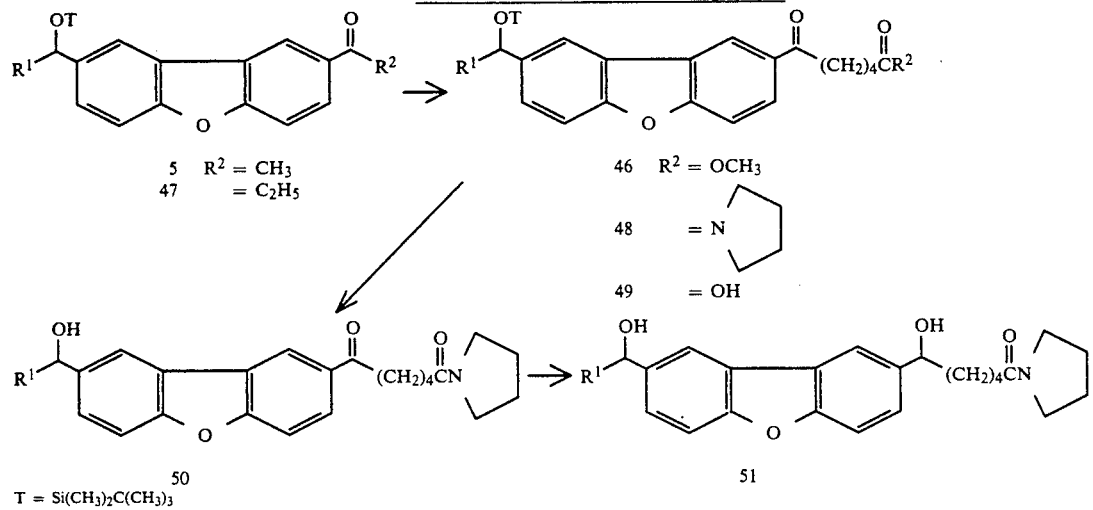

T = Si(CH₃)₂C(CH₃)₃

The following is a general description of the syntheses shown in Schemes I–IV:

2-Bromo-8-phenylacetyldibenzofuran (1, Scheme I) was prepared as previously reported by bromination of dibenzofuran (Buu-Hoï, Ng. Ph. and Royer, R. Rec. trav. chim. 1948, 67, 175; see also Mayer, F. and Krieger, W. Ber. 1922, 55, 1659 and Gilman, H.; Brown, G. E.; Bywater, W. G.; and Kirkpatrick, W. H. J. Am. Chem. Soc. 1934, 56, 2473), followed by Friedel-Crafts acylation with phenylacetyl chloride (Buu-Hoï, loc. cit.). The keto group in 1 was reduced most conveniently with a binary or complex hydride at 0°–100° C., preferably with sodium borohydride (NaBH₄) in a suitable protic solvent such as water, ethanol or other aliphatic alcohols or mixtures thereof at ambient temperatures to reflux, to give the alcohol 2. The preferred conditions were 2-propanol containing 4–10% water at reflux for a period of ca. 1 h. The alcohol function was then derivatized with a suitably inert protecting group, preferably the tertbutyldimethylsilyl (TBDMS) group, by reaction of 2 in N,N-dimethylformamide (DMF), or other aprotic polar solvent such as N,N-dimethylacetamide, methyl sulfoxide, tetramethylurea, and related compounds, with TBDMS-imidazole, or other TBDMS-N-alkylor arylamine or base conjugate, formed in situ by a general method (Corey, E. J. and Venkateswarlu, A. J. Am. Chem. Soc. 1972, 94, 6190), at 0°–100° C., preferably at ambient temperatures, to give 3. Alternative protecting groups include trialkylsilyl-, aryl dialkylsilyl ethers and variations thereof. Also any removable alkyl or aralkyl ether functional group may be employed. The organometallic derivative of 3, preferably the Grignard reagent, prepared from 3 by reaction with Mg turnings in an ethereal solvent, preferably refluxing tetrahydrofuran (THF), was reacted with acetaldehyde at -80°–100° C., preferably at 0°–25° C., to give upon workup under acidic conditions the ethanol derivative 4.

A. Compounds A, where n=1 (Scheme I), were prepared as follows.

1. Deblocking of the ether or silyl ether protected OH group in 4 with any reagent known to cleave ethers, especially silyl ethers, afforded the diol 6 (A, n=1, R¹=CH₂C₆H₅, R²=H). Among these reagents are acids, especially Lewis acids; bases, namely metal hydroxides, especially sodium hydroxide; fluoride salts, especially tetra-butylammonium fluoride (TBAF) or other organic-soluble fluorides, or fluorides rendered soluble via complexation, e. g., metal fluorides complexed with a crown ether, or fluoride salts rendered soluble in organic media via phase-transfer agents. The preferred conditons were tetrabutylammonium fluoride (TBAF) in tetrahydrofuran (THF) at ambient temperatures.

2. Alternatively, the alcohol 4 was oxidized with a suitable oxidant to give the methyl ketone 5. The preferred reagent is a chromium-based oxidant such as pyridinium chlorochromate in a medium of apolar organic solvent, preferably dichloromethane or chloroform at a temperature of 0°–100° C., preferably at ambient temperatures, although other oxidants in the same or in other solvents can be used. Neutralization of the acidic reagent or of acids produced during the reaction and workup is achieved with alumina, or the mixture is buffered with sodium acetate (Corey, E. J. and Suggs, J.

W. *Tetrahedron Lett.* 1975, 2647). A most convenient reagent is the pyridinium chlorochromate - alumina-supported reagent reported by Cheng, Y.-S.; Liu, W.-L. and Chen, S. Synthesis, 1980, 223.

Compound 5 was then converted with magnesium methyl carbonate (MMC) in DMF at 125° C. or thereabouts (Stiles, M. J. Am. Chem. Soc. 1959, 81, 2598) to the magnesium chelate (MMCadduct) of the enol of the $\beta$-keto-acid 7, from which the free acid 7 was obtained by acidification and immediate crystallization from heptane. Compound 7 was observed to decarboxylate rapidly upon standing in solution.

When freshly prepared 7 was reduced, preferably with a suitable binary or complex hydride, such as $NaBH_4$ in aqueous -alcoholic solution at 0°-100° C., preferably in aqueous 2-propanol at ambient temperatures, the hydroxy-acid 8 was obtained upon acidic workup. Removal of the TBDMS-protecting group, as previously described for the conversion of 4 to 6, e. g., using TBAF in THF, gave the diol-carboxylic acid 11 (A, n=1, $R^1=CH_2C_6H_5$, $R^2=CO_2H$).

3. Alternatively, the hydroxy-acid 8 was converted by standard procedures to the corresponding carboxylic acid ester, preferably to the methyl ester 9 via reaction of 8 with cold, ethereal diazomethane. Treatment of 9 with dimethylamine either neat or in an inert solvent at 0°-150° C., preferably in DMF in a sealed tube at 65° C. for 5 days, gave the hydroxy-amide 10. Deprotection of the protected OH group as in previous examples, e. g., with TBAF in THF, afforded the diol-amide 12 [A, n=1, $R^1 = CH_2C_6H_5$, $R^2=C(O)N(CH_3)_2$].

Compounds A, where n>1, were all prepared from the C-acetyl compound 5 by in situ C-alkylation of the MMC-adduct of 5 with the functionalized $\omega$-halides shown in Table II.

TABLE II

| | $\omega$-Halide Alkylating Reagents, $X(CH_2)_nY$ | |
|---|---|---|
| n | X | Y |
| 1 | Br | $CO_2C_2H_5$    $C(O)N(CH_3)_2$    CN    CON⟩ |
| 2 | Br or I | $CO_2CH_3$ |
| 2 | Cl + Br | $C(O)N(CH_3)_2$ |
| 3 | Br | $CO_2CH_3$ |

B. Compounds A, where n=2 (Scheme II) were prepared as follows.

1. When the MMC-adduct of 5, preformed in DMF, as in the previous example, was treated with ethyl bromoacetate, followed by acid workup, alkylation, as well as partial ester exchange and decarboxylation of the intermediate 13 occurred. Conditions include reaction of the MMC-adduct in a suitable inert solvent at 0°-200° C. with other $\alpha$-halogeno carboxylic acid esters. The preferred conditions were reaction of the MMC-adduct in dry DMF under nitrogen atmosphere with the methyl $\alpha$-iodo ester at 100° C. for 140 min. The mixture of esters 14a and 14b was converted to the hydroxy-keto-esters 18a and 18b by the deprotection methods previously discussed, e. g., with TBAF in THF. Reduction of the mixture of 18a and 18b, preferably with a suitable binary or complex hydride, such as with $NaBH_4$ in aqueous alcoholic solution, preferably in aqueous 2-propanol, gave a 2:1 mixture of the hydroxy-lactone 24 and the triol 25 (A, n=3, $R^1=CH_2C_6H_5$, $R^2=OH$), which were separated by column chromatography. The hydroxy-lactone 24 was converted to a diol-carboxylic acid alkali or alkaline-earth metal salt, preferably the sodium salt 26 (A, n =2, $R^1=CH_2C_6H_5$, $R^2=CO_2Na$), by treating an alcoholic, preferably a methanolic, solution of 24 with aqueous alkali or alkaline earth metal hydroxide, preferably sodium hydroxide.

2. The amides 22 and 23 [A, n=2, $R^1=CH_2C_6H_5$, and $R^2=C(O)N(CH_3)_2$ and $C(O)N(CH_2)_4$, respectively] were obtained by alkylation of the MMC-adduct of 5, preformed as previously described, with N,N-dimethylbromoacetamide and N-bromoacetpyrrolidine, or other suitably reactive $\alpha$-haloamides, especially the corresponding iodoamides to give the keto-amides 15 and 16, respectively. This alkylation reaction can be conducted between ambient temperatures and 250° C.; however, optimum conditions appear to be between 90° and 120° C. with any suitably reactive $\alpha$-haloamide to give amides of A (where n=2). Deblocking, as previously described, e. g., using TBAF in THF, gave the hydroxy-keto-amides 19 and 20, respectively. Reduction of the keto function in 19 or 20 was carried out, preferably with a suitable binary or complex hydride, such as with $NaBH_4$ in aqueous alcoholic solvent, preferably aqueous ethanol or 2-propanol at 0°-150° C., but optimally at 55°-85° C.

3. When the MMC-adduct of 5, prepared as described earlier, was treated with bromoacetonitrile or other haloacetonitrile, the keto-nitrile 17 was obtained under similar conditions.

C. The homologues A, where n=3 (Scheme III), could be obtained from the keto-ester 27, which was prepared by alkylation of the MMC-adduct of 5 with a suitable alkyl $\beta$-halopropionate, such as methyl 3-bromopropionate or, preferably, with methyl 3-iodopropionate. The conditions include use of a suitable inert solvent at 0°-200° C., preferably DMF at 50°-55° C., in a nitrogen atmosphere.

1. Removal of the TBDMS protecting group in 27 was accomplished under conditions described earlier, e. g., using TBAF in THF, to give the hydroxy-keto-ester 34. Hydrolysis of 34 with an aqueous alkali or alkaline earth metal hydroxide or other aqueous or alcoholic base, preferably aqueous sodium hydroxide in methanol, afforded 35 which was converted to the free acid 36 upon subsequent treatment with aqueous mineral acid. Reduction of the sodium salt 35, most conveniently with a binary or complex hydride, preferably with aqueous $NaBH_4$, at temperatures ranging from 0°-100° C., preferably at ambient temperatures to ca. 60° C., followed by acidification, gave a 1:1 mixture of the lactone 44 and the hydroxy-acid 45. The mixture of 44 and 45 was converted to the diol-carboxylic acid alkali or alkaline earth metal salt, preferably the sodium salt 40 [A, n=3, $R^1=CH_2C_6H_5$, $R^2=CO_2Na$] by reaction with aqueous alkali or alkaline earth hydroxide, preferably sodium hydroxide in methanol at ambient temperatures.

The ester 27 could be readily hydrolyzed to the keto-acid 30 with aqueous dilute mineral acid, preferably dilute hydrochloric acid.

2. The keto-amide 28 was obtained by reaction of the ketoester 27 with dimethylamine, either neat or in admixture with an inert solvent, at 0°-200° C., preferably neat in a sealed tube at 80°-95° C. for 5 days. Alternatively, reaction of the MMC-adduct of 5 with a N,N-dimethyl-3-halopropionamide (halo=Cl, Br, I) in a dry, inert solvent at 0°-200°, preferably in DMF at 105° C. for several hours, gave 28. Removal of the TBDMS protecting group in 28 using conditions established for similar reactions, e. g., with TBAF and THF, gave the hydroxy-keto-amide 37. The latter compound was reduced most conveniently with a suitable binary or complex hydride, preferably with NaBH$_4$ in aqueous alcoholic solvent at temperatures ranging from 0°-100° C. The optimum conditions were aqueous ethanol at ambient temperatures to ca. 60° C. to give the diol-amide 41 [A, n=3, R$^1$=CH$_2$C$_6$H$_5$, R$^2$=C(O)N(CH$_3$)$_2$].

3. Reaction of an alkyl or aryl ester, preferably the methyl ester 27, with pyrrolidine, either neat or in solution of an inert solvent, preferably neat and at reflux gave the ketoamide 29. Deblocking of the protected OH group in 29 using conditions described earlier, e. g., with TBAF in THF, afforded the hydroxy-keto-amide 38. The latter compound was reduced with a binary or complex hydride, preferably aqueous NaBH$_4$ in alcoholic solvent at temperatures of 0°-100° C., most appropriately in ethanol at ca. 55° C. for one hour or less, to give the diol-amide 42 [A, n=3, R$^1$=CH$_2$C$_6$H$_5$, R$^2$=C(O)N(CH$_2$)$_4$].

4. Hydrolysis of the ester 27 in a dilute aqueous or aqueous-alcoholic solution of alkaline earth metal hydroxide at 0°-200° C. gave the carboxylate salt. Preferred conditions were a boiling solution of methanolic aqueous sodium hydroxide which gave the sodium carboxylate 31. Conversion of the latter salt to the acid chloride 32 with oxalyl chloride and pyridine in benzene at ice-bath temperatures (Wilds, A. L. and Shunk, C. H. *J. Am. Chem. Soc.* 1948, 70, 2427), followed by reaction with an excess of morpholine, gave the ketone-amide 33. While these conditions for the direct production of the acid chloride 32 from the carboxylate salt are greatly favored, they may not be exclusive. Other reagents include thionyl chloride, phosphoryl chloride, or phosphorus trichloride (as well as their respective halogen analogues) as generally employed for the conversion of carboxylic acids or salts derived therefrom to acyl halides (see, for example, Buehler, C. A. and Pearson, D. E. "Survey of Organic Syntheses", Vol. 1, pp. 859-861). Removal of the TBDMS group in 33 was accomplished as previously described, e. g., using TBAF in THF, to give the hydroxy-ketoneamide 39. The latter compound was reduced to the diol-amide 43 [A, n=3, R$^2$=N(CH$_2$CH$_2$)$_2$O] using a binary or complex hydride, preferably NaBH$_4$ in aqueous or aqueous-alcoholic solvent at temperatures ranging from 0°-150° C. The optimum conditions were aqueous ethanol at or about 60° C.

D. The homologue A, where n=4, R$^1$=CH$_2$C$_6$H$_5$, and R$^2$=N(CH$_2$)$_4$ (Scheme IV) was prepared by alkylation of the MMC adduct of 5 with methyl 4-bromobutyrate, or a related 4-halobutyrate ester, to give the ester 46, which was converted to the amide 48 by heating with dry pyrollidine. Preferred conditions were similar to those mentioned earlier for the production of compounds 16 and 29. Alternatively, the ester 46 could be converted to the amide by a multistep process similar to that employed for the conversion of ester 2to the amide 33, q. v. Deblocking of the protected OH group in 48 was achieved as described earlier, e. g., using TBAF in THF, to give 50. Reduction of the ketone group in 50 was accomplished using a binary or complex hydride, preferably NaBH$_4$ in aqueous alcoholic solvent at 0°-150° C., e. g., in aqueous ethanol at or about 60° C., to give the diol-amide 51.

A large number of the novel dibenzofurans produced by the above procedures were assayed for anti-LTB$_4$ activity and were found to inhibit the activity of LTB$_4$ in vitro to a significant degree.

The present invention also comprehends pharmaceutical compositions containing as their active ingredient an effective amount, i.e., an amount effective to antagonize the LTB$_4$-mediated response being treated, of one or more of the substituted dibenzofurans in conventional pharmaceutical dosage forms. Such dosage forms include, but are not limited to, oral dosage forms such as capsules, tablets, caplets, lozenges, liquids, elixirs and suspensions; parenteral dosage forms such as injectable propylene glycol or isotonic saline solutions; and topical dosage forms including solutions in glycols or alcohol, lotions, creams, oily ointments, powders and aerosol sprays. All such dosage forms may include conventional carriers, diluents, excipients, binders and additives known to those skilled in the medicinal and pharmaceutical arts. Many examples of suitable dosage forms and vehicles are set forth in *Remington's Pharmaceutical Sciences,* 17th edition (1985).

The invention additionally encompasses a method of treating a human or animal patient to antagonize or counteract the effects of endogenous LTB$_4$ by administering to the patient pharmaceutical compositions as described in the preceding paragraph from one to four times daily. The human or animal patient might require such treatment for indications such as asthma, inflammatory and allergic disorders, immune system disorders, septic shock, transplant rejection, renal disease or a variety of other LTB$_4$-mediated conditions. Other specific indications would include psoriasis, arthritis, gout, cystic fibrosis, inflammatory bowel disease and pulmonary microembolization syndromes.

The following examples provide detailed illustrations of preparations of certain substituted dibenzofurans of the present invention together with biological assays of the novel compounds. These examples are not intended, however, to limit or restrict the scope of the invention in any way, and should not be construed as providing starting materials, reagents, synthetic methods or experimental conditions which must be utilized exclusively to practice the present invention.

EXAMPLE 1

1-[2-(8-Bromodibenzofuranyl)]-2-phenylethanol (2). A stirred mixture of 1 (16.14 g, 44.2 mmol) and 2-PrOH (65 mL) was heated to ca. 45° C., treated with a solution of NaBH$_4$ (0.65 g, 17.2 mmol) in H$_2$ (6.5 mL), and then refluxed for one h. Excess NaBH$_4$ was decomposed by acetone (2.5 mL), which was added to the partly cooled mixture. After 20 min, the upper layer was decanted, and the small lower layer was rinsed with 2-PrOH (3×4 mL). The combined 2-PrOH solutions were filtered and evaporated under reduced pressure to give 2 as a syrup from which minor impurities were removed by column chromatography (silica gel, 40 g, 70-230 mesh, Et$_2$O). Product fractions were evaporated to near dryness under reduced pressure. The residue was treated with heptane (50 mL), seeded, and swirled during the exothermic crystallization. Filtration, rinsing the solid with heptane (20 mL), and drying in vacuo for 4 h at 60° C. gave pure 2 (15.8 g, 97%), mp 94°-95.5° C. Even before it was solvent-free, the solid was observed to pick up electrical charges. A small second crop separated from the mother liquor as fluffy needles, mp 79°-81° C., that had the identical ¹H NMR (CDCl₃) spectrum as the major crop. TLC (silica gel, PhH): $R_f$ 0.3.

Anal. Calcd for $C_{20}H_{15}BrO_2$ [MW 367.24]: C, 65.41; H, 4.12; Br, 21.76. Found: C, 65.47; H, 4.15; Br, 21.82.

EXAMPLE 2

1-[2-(8-Bromodibenzofuranyl)]-1-tert-butyldimethylsiloxy-2-phenylethane (3). After it had stood overnight, a solution of 2 (10.8 g, 29.4 mmol), imidazole (5.0 g, 73 mmol), and tert-butylchlorodimethylsilane (5.32 g, 35.3 mmol) in DMF (35 mL, distilled from $CaH_2$ under reduced pressure, stored over 4 Å molecular sieves) was poured into ice/$H_2O$ (250 mL). The mixture was extracted with $Et_2O$ (2×60 mL). The extracts were washed with $H_2O$ (4×50 mL), dried ($MgSO_4$), and concentrated to a small volume to give a syrup which was dissolved in heptane (15 mL) and seeded. A first crop of 3 (7.65 g) separated overnight as colorless, hard kernels, which were filtered and rinsed with heptane (15 mL). Evaporation of solvent, addition of heptane (5 mL), and seeding gave a second crop (2.89 g) with the same mp, 68.5°–71° C.

Materials in the mother liquor were fractionated by chromatography on silica gel [75 g; 5% PhH/heptane (300 mL), then 20% PhH/heptane]. Early fractions contained contaminants; later fractions contained pure 3 (3.50 g; 99.6%, total), mp 68°–69.5° C., which readily picked up electrical charges. TLC (silica gel, 20% PhH/heptane): $R_f$ 0.75; GC (CP Sil 19-CB, 10 m, 5 psi He, 230° C.): $R_t$ 16.07 min.

Anal. Calcd for $C_{26}H_{29}BrO_2Si$ [MW 481.50]: C, 64.86; H, 6.07; Br, 16.59. Found: C, 64.74; H, 6.09; Br, 16.51.

EXAMPLE 3

1-[2-[8-(1-tert-Butyldimethylsiloxy)-2-phenylethyl]-dibenzofuranyl]ethanol (4). EtBr, from which the initiator EtMgBr was prepared, was washed sequentially with conc. $H_2SO_4$ until the wash liquid was colorless, $H_2O$, aqueous $Na_2CO_3$, and $H_2O$, dried ($MgSO_4$), distilled from $P_2O_5$, and stored over 4 Å molecular sieves.

A dry, 3-neck flask, equipped with a condenser topped with a Drierite-filled tube, and containing Mg turnings (0.29 g, 12 mmol), was flushed with dry $N_2$. When 3 mL of a solution of EtBr (1.14 g, 10.5 mmol) in dry THF (10.0 mL) was added, spontaneous exothermic reaction occurred. The remainder of the EtBr solution was added to the stirred mixture during ca. 15 min at that rate at which gentle reflux occurred. The mixture was then heated to maintain reflux for 45 min and then diluted with THF (10 mL). Such EtMgBr solutions, kept in septum-stoppered flasks, retained excellent initiator properties for at least one week.

For the synthesis of 4, Mg (0.35 g, 14 mmol, 1.7 equiv) was treated with the above EtMgBr solution (5.0 mL), followed by 3 (4.0 g, 8.3 mmol; dried in vacuo) dissolved in THF (20 mL). The stirred mixture was gently refluxed for 2.5 h under $N_2$, cooled to ca. 0° C., and treated dropwise during ca. 3 min with a solution (6.5 mL, 2.25 M) of $CH_3CHO$ (14.3 mmol, 1.7 equiv) in THF that had been kept over Drierite. The mixture was stirred overnight at ambient temperatures and was then treated with aqueous saturated $NH_4Cl$ (10 mL). After 0.5 h the THF layer was decanted, and the residual organic materials in the lower layer were extracted with $Et_2O$. The combined THF and $Et_2O$ solutions were dried ($MgSO_4$), and the solvent was evaporated under reduced pressure to give a syrup that was purified by column chromatography (silica gel, 180 g, 5% $Et_2O$/PhH). Early fractions contained side-products; later fractions gave 4 as a syrup (3.68 g) that contained one mole of PhH according to a ¹H NMR spectrum. The yield of pure 4 was 3.13 g, 84%. TLC (silica gel/PhH): $R_f$ 0.3. For elemental analysis, a sample was dried in vacuo at 65° C.

Anal. Calcd for $C_{28}H_{34}O_3Si$ [MW 446.67]: C, 75.29; H, 7.67. Found: C, 75.42; H, 7.76.

Inferior results were obtained when $BrCH_2CH_2Br$ was used to initiate the reaction of Mg with 3 or when slightly impure 3 was used.

EXAMPLE 4

1-[2-[8-(1-Hydroxy)-2-phenylethyl]dibenzofuranyl]ethanol (6). A solution of 4 (0.25, 0.56 mmol), THF (6.5 mL), and $Bu_4NF$ (0.73 mL, 1 M in THF) was left overnight and then percolated through silica gel (4.5 g) with THF (20 mL). Evaporation of solvent gave a syrup that was fractionated by chromatography (silica gel, 17 g, $CHCl_3$); early fractions contained contaminants, late fractions gave pure 6 (ca. 0.19 g, 100%) as a tough syrup, which was dried in vacuo, 40° C., 20 h; TLC (silica gel, $CHCl_3$): $R_f$ 0.1. Attempts to crystallize this mixture of diastereomers from $Et_2O$ failed.

Anal. Calcd for $C_{22}H_{20}O_3$ [MW 332.40]: C, 79.49; H, 6.06. Found: C, 79.23; H, 6.16.

EXAMPLE 5

1-[2-[8-(1-tert-Butyldimethylsiloxy)-2-phenylethyl]-dibenzofuranyl]ethanone (5). To a solution of 4 (3.79 g,.ca. 7.8 mmol, containing ca. 0.3 g PhH) in $CH_2Cl_2$ (80 mL) were added alumina (10 g) and pyridinium chlorochromate (3.4 g, 16 mmol, 2 equiv). The mixture, protected with a Drierite-filled tube, was stirred overnight. Solids were removed by filtration and rinsed with $CH_2Cl_2$ and PhH. The combined filtrate and rinsings were evaporated under reduced pressure. The PhH-soluble portion of the residue was percolated through alumina (60 g) with PhH; evaporation of solvent gave a colorless syrup, which was dissolved in heptane (ca. 3 mL) and seeded. Evaporation of heptane afforded pure 5 (3.00 g, 93%), mp 93°–94.5° C.; TLC (silica gel/PhH): $R_f$ 0.7.

Anal. Calcd for $C_{28}H_{32}O_3Si$ [MW 444.65]: C, 75.64; H, 7.25. Found: C, 75.73; H, 7.31.

EXAMPLE 6

3-[2-[8-(1-tert-butyldimethylsiloxy)-2-phenylethyl]-dibenzofuranyl]-3-oxopropionic Acid (7). A stirred solution of 5 (0.78 g, 1.75 mmol) in DMF (3.0 mL, distilled from $CaH_2$ under reduced pressure, stored over 4 Å sieves) and magnesium methyl carbonate (15 mL, 2 M in DMF, 17 equiv), under dry $N_2$, was heated at 125° C. (external) for 110 min, cooled, poured into ice and water (ca. 60 g) and treated with aqueous HCl (45 mL, 1.4 N) to pH <2. Since, after it had been shaken with $Et_2O$ (60 mL), the solution had pH 4, additional HCl (1.5 mL) was added to achieve pH ca. 2. The organic layer, combined with a second ethereal extract (25 mL), was washed with ice-water, dried ($MgSO_4$), and the solvent was evaporated under reduced pressure to give a residue that contained 7 (78%) and 5 (22%) according to its ¹H NMR spectrum. Dissolution of the product in heptane (5 mL), seeding, filtration, and rinsing of the solid with heptane (5 mL) gave pure 7 (0.58 g, 68%), mp 105°–106.5° C. dec (variable); TLC (silica gel, 20% $MeOH/CHCl_3$): $R_f$ ca. 0.4.

Anal Calcd for $C_{29}H_{32}O_5Si$ [MW 488.66]: C, 71.28; H, 6.60. Found: C, 71.20; H, 6.66.

EXAMPLE 7

3-[2-[8-(1-tert-butyldimethylsiloxy)-2-phenylethyl]-dibenzofuranyl]-3-hydroxypropionic Acid (8). Immediately after its preparation, compound 7 (0.57 g, 1.17 mmol) was suspended in 2-PrOH (20 mL), stirred, and treated dropwise with a solution of $NaBH_4$ (0.25 g, 6.6 mmol) in water (1.0 mL). Hydrogen evolved, the mixture became warm, and another solid separated. Spattered materials were rinsed down with 2-PrOH (5 mL), and the mixture was stirred for 3 h and then treated with acetone (5 mL) to decompose excess $NaBH_4$. After 0.5 h, most of the volatiles were evaporated under reduced pressure. The residue was treated with ice and water and sufficient aqueous HCl (1.4 N, ca. 5.0 mL) so that the aqueous layer had pH 2 after extraction with $Et_2O$. The organic layer, combined with a second ethereal extract, was washed with ice-water, dried ($MgSO_4$), and stripped of solvent to give a syrup that was fractionated on silica gel (30 g). $CHCl_3$ eluted small amounts of 4 (formed by reduction of the decarboxylation product 5); 5 and 10% $MeOH/CHCl_3$ gave 8 as a syrup (0.5 g, 89%); TLC (silica gel, 20% $MeOH/CHCl_3$) $R_f$ ca. 0.3. On drying in vacuo at 40° C. overnight, the product hardened to a glass.

Anal. Calcd for $C_{29}H_{34}O_5Si$ [MW 490.68]: C, 70.99; H, 6.98. Found: C, 70.84; H, 7.00.

EXAMPLE 8

3-[2-[8-(1-Hydroxy)-2-phenylethyl]dibenzofuranyl]-3-hydroxypropionic Acid (11). A solution of 8 (0.42 g, 0.86 mmol) in THF (3 mL) and $Bu_4NF$ (1.35 mL, 1 M, 1.6 equiv) was concentrated to a small volume with a stream of $N_2$, protected with a Drieritefilled tube, and left to stand for 5 days. Percolation through silica gel (7 g) with THF gave a fraction A (0.18 g) containing the $Bu_4N^+$ salt of 11 as well as tert-butyldimethylsilyl compounds ($^1H$ NMR spectral analysis). Elution with 20% $MeOH/CHCl_3$ gave a fraction B (0.54 g) which contained, aside from the $Bu_4N^+$ salt of 11, inorganic $Bu_4N^+$ salts. Treatment of B with $H_2O$ (5 mL) and HCl (0.54 mL, 1.4 N) gave an aqueous solution C and a gum which was rinsed with $H_2O$ and dried by treatment with PhH and evaporation under reduced pressure. The gum (0.25 g) then consisted of a mixture of 11 and ca. 0.5 mol of a $Bu_4N^+$ salt. Chromatography (silica gel, 7 g, 2% $MeOH/CHCl_3$) gave 11 (60 mg) as a syrup, which was subsequently treated with $CHCl_3$. After the solution had been clarified by filtration, a solid gradually formed as the solvent evaporated. When the solid was then treated with $Et_2O$, its appearance gradually changed. Filtration after several h gave a first crop of pure 11 (55 mg).

Further elution of the column with 15% $MeOH/CHCl_3$ gave a solid (0.13 g) that retained the $Bu_4N^+$ species. The solid, combined with fraction A, was dissolved in MeOH, treated with aqueous HCl (0.9 mL, 1.4 N) followed at once by $H_2O$ (ca. 40 mL) to give a milky solution from which a gum gradually separated. Decantation, rinsing with $H_2O$, and azeotropic drying with PhH under reduced pressure gave a gum which was dissolved in $Et_2O$. After clarification by filtration, the solution slowly deposited 11 (crop 2, 135 mg). [It is believed that crystallization occurs only as $H_2O$ is gradually absorbed from the atmosphere by the ethereal solution; rapid evaporation of $Et_2O$, even in the presence of seed crystals, gave a gum.]

The aqueous HCl solution C (above) deposited additional gum after standing overnight. The gum was treated as above (the liquid was decanted and washed with $H_2O$, PhH was added and evaporated, then $Et_2O$ was added and the mixture was left to crystallize overnight) to give a third crop (43.4 mg; total, 72%). The crystalline material, after drying overnight at 65° C. in vacuo, partially melted >85°, partially resolidified at higher temperatures, and subsequently formed a clear, gas-containing melt 149°–159° C. [TLC of the melt showed that extensive decomposition had occurred.]

Anal. Calcd for $C_{23}H_{20}O_5 \cdot H_2O$ [MW 394.43]: C, 70.04; H, 5.62. Found: C, 70.23; H, 5.59.

EXAMPLE 9

Methyl 3-[2-[8-(1-tert-Butyldimethylsiloxy)-2-phenylethyl]dibenzofuranyl]-3-hydroxypropionate (9). An ice-cold solution of the acid 8 (ca. 0.76 g, 1.55 mmol) in $Et_2O$ (8 mL) was treated dropwise during ca. 1 min with cold, ethereal $CH_2N_2$ [prepared from N-nitrosomethylurea (Organic Syntheses, Coll. Vol. II, pp. 461 and 166, method in Note 3 therein)]until the yellow $CH_2N_2$ color persisted. After 30 min, the solution was dried ($MgSO_4$), filtered, and evaporated to dryness. The residue was purified by chromatography on silica gel (40 g), first eluting with $CHCl_3$; 2% $MeOH/CHCl_3$ gave 9 as a syrup (0.9 g) that contained ca. 30% CHCl3; TLC (silica gel, CHCl3) $R_f$ 0.2. A portion was dried in vacuo at 80° C. for 22 h.

Anal. Calcd for $C_{30}H_{36}O_5Si$ [MW 504.7]: C, 71.39; H, 7.19. Found: C, 71.44; H, 7.20.

EXAMPLE 10

N,N-Dimethyl-3-[2-[8-(1-tert-butyldimethylsiloxy)-2-phenylethyl]dibenzofuranyl]-3-hydroxypropanamide (10). A solution of the ester 9 (ca. 0.6 g, 1.19 mmol) in dry DMF (8 mL) and dimethylamine (5 mL, dried over 4 Å molecular sieves) was heated in a sealed glass bottle at 65° C. for 5 days. The cooled solution was poured into ice + $H_2O$ (50 g) to give a milky suspension, which was acidified to pH 4 with aqueous HCl (29 mL, 1.4 N) and then contained a semisolid gum. A $CHCl_3$ solution (30 mL) of the gum was dried ($MgSO_4$) and evaporated under reduced pressure to give a syrup, which was fractionated on silica gel (50 g). Eluates of $CHCl_3$ (200 mL) and 2% $Et_2O/CHCl_3$ (250 mL) were discarded. Additional 2% $Et_2O/CHCl_3$ (50 mL) and 5% $Et_2O/CHCl_3$ (100 mL) eluted 9 (0.19 g); later fractions of 5 and 10% $Et_2O/CHCl_3$ (200 and 100 mL, respectively) gave 10 (0.36 g, 86% based on nonrecovered 9); TLC (silica gel, 15% $Et_2O/CHCl_3$): $R_f$ 0.4. The syrup failed to crystallize from $Et_2O$. A portion of 10 was dried at 65° C., 0.1 torr, 24 h, to give a tough syrup.

Anal. Calcd for $C_{31}H_{29}NO_4Si$ + 0.33 $Et_2O$ [MW 539.98]: C, 71.62; H, 7.84; N, 2.59. Found: C, 71.50 & 71.42; H, 7.63 & 7.65; N, 2.58.

EXAMPLE 11

N,N-Dimethyl-3-[2-[8-(1-hydroxy)-2-phenylethyl]-dibenzofuranyl]-3-hydroxypropanamide (12). A solution of 10 (0.32 g, 0.62 mmol) in THF (2 mL) and $Bu_4NF$ (1.2 mL, 1.1 M in THF, 2.1 equiv) was stirred under $N_2$ overnight. Addition of ice + $H_2O$ gave a gum which, after the aqueous phase had been decanted, was dissolved in $CHCl_3$ (30 mL). The solution was washed with ice-water (2×20 mL), dried ($MgSO_4$), and evaporated under reduced pressure to give a syrup, which was fractionated on silica gel (35 g) first eluting with CHCl$_3$ (100 mL); 10% MeOH/CHCl$_3$ (100 mL) eluted 12 contaminated with tert-butyldimethylsilyl compounds. On rechromatography (silica gel, 40 g), 1% MeOH/CHCl$_3$ gave contaminants; 10% MeOH/CHCl$_3$ eluted 12; TLC (silica gel, ca. 8% MeOH/CHCl$_3$): R$_f$ 0.2. A CHCl$_3$ solution of 12 was evaporated, and the residue was then dried for 16.5 h, 0.1 torr, to give 12 as a froth that retained 4.4% CHCl$_3$ (0.24 g; 92%).

Anal. Calcd for C$_{25}$H$_{25}$NO$_4$ + 0.15 CHCl$_3$ [MW 421.89]: C, 71.61; H, 6.01; N, 3.32. Found: C, 71.63 & 71.59; H, 6.11 & 6.16; N, 3.31.

EXAMPLE 12

Methyl and Ethyl 4-[2-[8-(1-tert-Butyldimethylsiloxy)-2-phenylethyl]dibenzofuranyl]-4-oxobutanoate, 14a and 14b. Compound 5 (0.74 g, 1.66 mmol), dissolved in dry DMF (3 mL), was converted to its magnesium carboxylate adduct by heating with magnesium methyl carbonate (MMC, 15 mL, 2 M, 18 equiv) under dry N$_2$ at 125° C. for 110 min. The cooled solution was treated with ethyl bromoacetate (0.83 g, 5 mmol, 3 equiv), dissolved in dry DMF (1 mL), and heated at 100° C. for 140 min. The solution was cooled to ca. 50° C., poured into water containing ice (ca. 100 g), and treated with aqueous HCl (40 mL, 1.4 M), which caused the dissolution of the initial voluminous precipitate and the separation of a brownish solid. Extraction with Et$_2$O (2×25 mL), drying the extract (MgSO$_4$) and evaporation under reduced pressure gave an orange syrup, which was subjected to chromatography on silica gel (65 g). PhH eluted trace amounts of impurities and 5, followed by mixtures of the ethyl and methyl esters, 14b and 14a. 5, 10 and 25% CHCl$_3$/PhH (200 mL, each) continued to elute such mixtures (0.66 g total, ca. 80%); TLC (silica gel, 2 × developed with PhH): R$_f$ 0.45 and 0.4, respectively. The last fractions, which were greatly enriched in the methyl ester (14a), gave a gum (0.23 g), which on treatment with heptane ultimately crystallized and then had mp 85.5°–87° C. The gum was subjected to elemental analysis.

Anal. Calcd for C$_{31}$H$_{36}$O$_5$Si [MW 516.72]: C, 72.06; H, 7.02. Found: C, 72.10; H, 7.03.

EXAMPLE 13

Methyl and Ethyl 4-[2-[8-(1-Hydroxy)-2-phenylethyl]dibenzofuranyl]-4-oxobutanoate, 18a and 18b. The TBDMS protecting group in the esters 14a and 14b (0.44 g) was removed as in Example 4. The crude products were fractioned on silica gel (8 g); PhH eluted silicon compounds together with a portion of the esters 18a and 18b (ca. 10%), 10 and 20% Et$_2$O/PhH eluted the remainder of 18a and 18b (ca. 70%). A sample of pure methyl ester 18a, mp 103°–105° C., was obtained by crystallization (Et$_2$O) of the material in the last fraction.

Anal. Calcd for C$_{25}$H$_{22}$O$_5$[MW 402.45]C, 74.61; H, 5.51. Found: C, 74.65; H, 5.58.

EXAMPLE 14

4-[2-[8-(1-Hydroxy)-2-phenylethyl]dibenzofuranyl]-1,4-dihydroxybutane (25) and 4-[2-[8-(1 Hydroxy)-2-phenylethyl]dibenzofuranyl]-4-hydroxybutanoic lactone (24). A warm solution of the mixture of esters 18a and 18b (0.24 g) in 2-PrOH (5 mL) was cooled, treated with aqueous NaBH$_4$ (22 mg, 1 molar equiv, in 0.25 mL), and stirred for 90 min. Acetone (0.5 mL) was added, stirring was continued for 30 min, and the solution was decanted from a small lower layer, which was then treated with H$_2$O and extracted with Et$_2$O. The 2-PrOH and Et$_2$O solutions were combined, dried (MgSO$_4$), and evaporated under reduced pressure. The residue was percolated through silica gel (8 g) with 2% MeOH/CHCl$_3$, which gave the lactone 24 [110 mg, 50%; TLC (silica gel, ca. 4% MeOH/CHCl$_3$): R$_f$ 0.5] and traces of the dihydroxy esters 21a and 21b (TLC: R$_f$ 0.3); 5% MeOH/CHCl$_3$ eluted the triol 25 (50 mg), obtained as a syrup, which, on drying at 65° C. in vacuo overnight, was converted into a hygroscopic, hard glass (41.7 mg, 19%); TLC (silica gel, 10% MeOH/CHCl$_3$): R$_f$ 0.25.

Anal. Calcd for C$_{24}$H$_{24}$O$_4$ + 0.41 H$_2$O [MW 383.84]: C, 75.10; H, 6.52. Found: C, 75.08; H, 6.60.

EXAMPLE 15

Sodium 4-[2-[8-(1-Hydroxy)-2-phenylethyl]dibenzofuranyl]-4-hydroxybutanoate (26). A stirred, methanolic solution (2 mL) of the lactone 24 (100 mg, ca. 0.27 mmol), contaminated with small amounts of the esters 21, was treated dropwise with aqueous NaOH (1.3 mL, 0.58 M, ca. 2.8 equiv). After 10 min the solution was concentrated under reduced pressure to give a thick, yellow syrup, which was fractionated on DIAION HP-20 resin (Mitsubishi Chemical Co., 30 mL of the beads, washed with MeOH and then with H$_2$O). After sequential elution with H$_2$O (50 mL), 5, 10, and 25% MeOH/H$_2$O (30 mL each), 50% MeOH/H$_2$O (ca. 120 mL) eluted 26 (90 mg, ca. 72%). An aqueous solution of the syrup was clarified by filtration and stripped of volatiles under reduced pressure. When the residual syrup was treated with MeOH, a small amount of flocculent solid separated and was removed by filtration. The solvent was evaporated, and the residue was then dried at 65° C., 0.1 torr, for 24 h.

Anal. Calcd for C$_{24}$H$_{21}$O$_5$Na + 2 H$_2$O + 2.5% inert material [MW 460.15]: C, 62.64; H, 5.48. Found: C, 62.68 & 62.57; H, 5.42 & 5.47.

EXAMPLE 16

N,N-Dimethyl-4-[2-[8-(1-tert-butyldimethylsiloxy)-2-phenylethyl]dibenzofuranyl]-4-oxobutanamide (15). A solution of the MMC adduct, prepared from 5 (0.78 g, 1.75 mmol) as in Example 6, but with less magnesium methyl carbonate (7.5 equiv), was treated with N,N-dimethylbromoacetamide (0.95 g, 5.7 mmol, 3.3 equiv) dissolved in dry DMF (0.9 mL) and then heated at 120° C. for 1 h. The cooled solution was poured into ice + H$_2$O (75 g) and acidified with HCl (1.4 M) to pH ~3. The crude product, isolated by filtration, was purified by chromatography on silica gel (50 g) with CHCl$_3$. Early fractions contained side-products and 5 (ca. 0.05 g); evaporation of later fractions gave a syrup that failed to crystallize from heptane and was dried in vacuo at 65° C., 3 h, to give 15 (0.68 g; 78%, based on unrecovered 5); TLC (silica gel/CHCl$_3$): R$_f$ ca. 0.4.

Anal. Calcd for C$_{32}$H$_{39}$NO$_4$Si [MW 529.76]: C, 72.55; H, 7.42; N, 2.64. Found: C, 72.51; H, 7.48; N, 2.55.

EXAMPLE 17

N,N-Dimethyl-4-[2-[8-(1-hydroxy)-2-phenylethyl]-dibenzofuranyl]-4- oxobutanamide (19). The TBDMS group was removed from 15 (ca. 0.63 g, 1.2 mmol) as in Example 11. The product was purified by chromatography on silica gel (50 g), first eluting with CHCl$_3$ (175 mL); 5% MeOH/CHCl₃ eluted 19, which gradually crystallized from Et₂O to give a colorless solid, mp 136°–137° C.; TLC (silica gel, ca. 5% MeOH/CHCl₃): $R_f$ 0.3. After drying at 65° C., 0.1 torr, 7 h, the solid (0.44 g, 88%) retained some Et₂O (¹H NMR spectral analysis).

Anal. Calcd for $C_{26}H_{25}NO_4$ + 0.05 $C_4H_{10}O$ [MW 419.2]: C, 75.07; H, 6.13; N, 3.34. Found: C, 75.06; H, 6.07; N, 3.36.

EXAMPLE 18

N,N-Dimethyl-4-[2-[8-(1-hydroxy)-2-phenylethyl]-dibenzofuran-2-yl]-4-hydroxybutanamide (22). A warm ethanolic solution (8 mL) of 19 (0.20 g, 0.48 mmol) was treated with NaBH₄ (28.0 mg, 0.74 mmol, 1.5 molar equiv) dissolved in H₂O (0.2 mL) and stirred for 30 min at 55° C. The mixture was cooled, acetone (0.5 mL) was added, and stirring was continued for 30 min. Concentration of the solution under reduced pressure gave a residue, which was treated with ice + H₂O (30 g), acidified to pH 3, and extracted with CHCl₃ (4×20 mL). The extracts were dried (MgSO₄), evaporated at 12 torr and then dried at 0.1 torr, 40° C., 2 d, to give 22 as a froth (0.19 g, 96%), devoid of CHCl₃; TLC (silLca gel, ca. 15% MeOH/CHCl₃): $R_f$ 0.5.

Anal. Calcd for $C_{26}H_{27}NO_4$ + 0.7 $H_2O$ [MW 430.12]: C, 72.60; H, 6.66; N, 3.26. Found: C, 72.56 & 72.51; H, 6.55 & 6.58; N, 3.15; (Cl, O).

EXAMPLE 19

N-[4-[2-[8-(1-tert-Butyldimethylsiloxy)-2-phenylethyl]dibenzofuranyl]-4-oxobutanoyl]pyrrolidine (16). N-Bromoacetylpyrrolidine was prepared as follows: A stirred solution of bromoacetylbromide (3.5 mL, 40 mmol) in CHCl₃ (30 mL, percolated through alumina to remove EtOH), cooled to ca. 0° C. and protected with a Drierite-filled tube, was treated dropwise during 10 min with a solution of pyrrolidine (6.0 mL, 73 mmol, 1.8 equiv) in CHCl₃ (20 mL). After an additional 30 min, the solution was washed with ice-water (4×50 mL) and aqueous NaHCO₃ (20 mL, 0.02 M), dried (MgSO₄), and evaporated under reduced pressure to give the bromoamide (5.58 g, 80%) as a thin, yellowish liquid that solidified at −17° C.

The magnesium carboxylate adduct of compound 5 (0.78 g, 1.75 mmol) was prepared as described in Example 6, except that less magnesium methyl carbonate was used (8.8 mL, 2 M in DMF, 10 equiv). A solution of N-bromoacetyl pyrrolidine (1.0 g, 5.2 mmol, 3 equiv) in DMF (1 mL) was added, and the solution was then heated at 100° C. for 1 h under N₂, at which time no further CO₂ evolved. The cooled solution was poured into ice-water and treated with aqueous HCl (23 mL, 1.4 M) to pH 4. Since the pH increased after the mixture had been extracted with CHCl₃ (40 mL), presumably because basic Mg salts had been trapped in the gummy water insoluble product, additional HCl was added to give pH 4 after shaking with the CHCl₃. The organic layer was washed with H₂O, dried (MgSO₄), and stripped of volatiles under reduced pressure to give a syrup that was fractionated by column chromatography (silica gel, 35 g). PhH eluted trace amounts of a side product, 10% Et₂O/PhH eluted unreacted 5, 50% Et₂O/PhH and Et₂O gave the amide 16 as a syrup, which on dissolution in heptane and scratching was converted into a flocculent, colorless solid (0.75 g, 76%), mp 91°–101° C.; TLC (silica gel, Et₂O): $R_f$ 0.4. Drying at 65° C. in vacuo gave a hard glass that, when broken up by scraping, picked up static electricity.

Anal. Calcd for $C_{34}H_{41}NO_4Si$ [MW 555.8]: C, 73.48; H, 7.44; N, 2.52. Found: C, 73.52; H, 7.45; N, 2.52.

EXAMPLE 20

N-[4-[2-[8-(1-Hydroxy)-2-phenylethyl]dibenzofuranyl]-4-oxobutanoyl]pyrrolidine (20). A solution of compound 16 (0.70 g, 1.26 mmol) in THF (2.8 mL) and Bu₄NF (2.3 mL, 1 M in THF) under N₂ was kept at ambient temperatures for 3.5 h and then at 4° C. overnight. Addition of ice and H₂O gave a gum, which was extracted with CHCl₃ (30 mL). The extract was washed with ice-H₂O (2×20 mL), dried (MgSO₄), and the solvent was evaporated under reduced pressure to give a syrup, which, on treatment with heptane (15 mL), was converted to a solid (0.55 g, 98%), mp 144°–145° C.; TLC (silica gel, 10% MeOH/CHCl₃): $R_f$ 0.5.

Anal. Calcd for $C_{28}H_{27}NO_4$ [MW 441.54]: C, 76.17; H, 6.16; N, 3.17. Found: C, 76.07; H, 6.18; N, 3.16.

EXAMPLE 21

N-[4-[2-[8-(1-Hydroxy)-2-phenylethyl]dibenzofuranyl]-4-hydroxybutanoyl]pyrrolidine (23). The ketone 20 (0.50 g) was insoluble in hot 2-PrOH (5 mL) but dissolved when CHCl₃ (9 mL) was also added. The cooled solution was treated with NaBH₄ (44 mg, 1.05 molar equiv) dissolved in H₂O(0.25 mL), vigorously stirred overnight, and then boiled for 15 min to complete the reduction. The solution was cooled, acetone (1.5 mL) was added, stirring was continued for 30 min, and H₂O (10 mL) and CHCl₃ (15 mL) were then added to give two milky layers. The aqueous layer was extracted with another portion of CHCl₃ (10 mL), and the combined CHCl₃ solutions were washed with H₂O (20 mL), dried (MgSO₄), and evaporated under reduced pressure to give a syrup, which was purified by chromatography (silica gel, 35 g), eluting with 2-and 5% MeOH/CHCl₃. The product, 23, after drying overnight, 0.1 torr, was a colorless, hard froth (0.49 g, 96%), mp sags ~50° C. to become a thick syrup; TLC (silica gel, 10% MeOH/CHCl₃): $R_f$ 0.3.

Anal. Calcd for $C_{28}H_{29}NO_4$ + 0.19 CHCl₃ [MW 443.55]: C, 72.62; H, 6.31; N, 3.00; Cl, 4.34. Found: C, 72.65 & 72.60; H, 6.38 & 6.38; N, 2.98 & 2.97; Cl, 4.33.

EXAMPLE 22

4-[2-[8-(1-tert-Butyldimethylsilyl)-2-phenylethyl]-dibenzofuranyl]-4-oxobutanenitrile (17). The MMC adduct, prepared from 5 (0.78 g, 1.75 mmol) as in Example 16, was heated with bromoacetonitrile (0.37 mL, 5.3 mmol, 3 equiv) at 90° C. for 2 h and left overnight at ambient temperatures. After the usual aqueous acid workup, extraction with CHCl₃ (2×25 mL, then 15 mL), and washing the extract with ice-water (25 mL), drying (MgSO₄), and evaporation of the solvent under reduced pressure, a liquid (5 g) was obtained, which was dissolved in Et₂O (40 mL). The solution was washed with ice-water (40 and 25 mL), dried (MgSO₄), and evaporated to give a syrup, which was fractionated on silica gel (60 g). PhH eluted traces of a side-product, followed by 5 (0.15 g) and 17, which was recrystallized from Et₂O to give a colorless solid (0.37 g, 54%, based on nonrecovered 5), mp 139°–140° C., which picks up static electricity; TLC (silica gel, PhH): $R_f$ ca. 0.4.

Anal. Calcd for $C_{30}H_{33}NO_3Si$ [MW 483.69]: C, 74.50; H, 6.88; N, 2.90. Found: C, 74.41; H, 6.92; N, 2.86.

EXAMPLE 23

Methyl 5-[2-[8-(1-tert-Butyldimethylsiloxy)-2-phenylethyl]dibenzofuranyl]-5-oxopentanoate (27). Method A. Compound 5 (3.1 g, 7 mmol) was converted to its MMC-adduct as in Example 19. Methyl 3-bromopropionate (6.2 mL, 15 mmol, 8.2 equiv) was added, and the solution was heated at 50°–55° C. for 21 h and then at 100° C. for 2 h. The cooled solution was poured into ice + water (150 g), acidified (1.4 N HCl, ca. 50 mL) to pH 4, and extracted with $Et_2O$ (125 mL). The extract was washed with ice-water (50 mL), dried ($MgSO_4$), and evaporated under reduced pressure. The residue was fractionated by column chromatography (silica gel, 250 g); PhH eluted small amounts of side-products, followed by 5 (1.57 g, 51%); 5% $Et_2O$/PhH eluted 27 (1.87 g, containing 1 molequiv of PhH, i.e., 1.63 g of pure 27 or 89% based on nonrecovered 5) as a syrup which, on treatment with hexane and seeding, gradually changed to a solid, mp 68°–72° C.; TLC (silica gel, PhH): $R_f$ 0.35.

Anal. Calcd for $C_{32}H_{38}O_5Si$ [MW 530.74]: C, 72.42; H, 7.22. Found: C, 72.55; H, 7.28.

Method B. The MMC-adduct formation, its alkylation, and the isolation of crude product were carried out as in Method A except that the reaction was scaled down to 1.64 g of 5 and methyl 3-iodopropionate was used in lieu of the bromo derivative.

Methyl 3-iodopropionate was prepared by treating a stirred acetone solution (20 mL) of methyl 3-bromopropionate (3.3 mL, 30.2 mmol) with NaI (5.8 g, 38.7 mmol) at ambient temperatures. After 2 h, the mixture was heated at 50° C. for 45 min, cooled and filtered. The filtrate was concentrated under reduced pressure, diluted with $Et_2O$ (30 mL), extracted with ice-cold $H_2O$ (2×20 mL), dried ($MgSO_4$), and the solvent was evaporated under reduced pressure to give a liquid (6.57 g, ca. 95%) consisting of the iodo-ester (95%) and the bromoester (5%) ($^1$H-NMR spectral analysis), which was used without further purification.

A solution of the crude alkylation product 27 (1.97 g) in heptane (5 mL) was evaporated under reduced pressure and ca. 55° C. (to remove residual $CH_2=CHCO_2CH_3$). Crystallization from heptane (3 mL) gave 27 (0.90 g), mp 69°–72° C. The material in the mother liquor was percolated through silica gel (75 g) with PhH, which eluted several side products as well as unreacted 5 (ca. 26%). 5% $Et_2O$/PhH eluted the product (0.47 g), which was recrystallized from heptane (4 mL) to give pure 27 (0.28 g; total, 78%, based on non-recovered 5); TLC (silica gel, PhH) $R_f$ 0.35.

EXAMPLE 24

Methyl 5-[2-[8-(1-Hydroxy)-2-phenylethyl]dibenzofuranyl]-5-oxopentanoate (34). A solution of 27 (0.41 g, 0.77 mmol) in dry THF (1.5 mL) and $Bu_4NF$ (1.5 mL, 1 M in THF, 1.9 equiv) was stirred under $N_2$ for 2.5 h, at the end of which time none of 27 remained (TLC analysis). The solution was diluted with $CHCl_3$ (25 mL), washed with $H_2O$ (2×25 mL), dried ($MgSO_4$), and evaporated under reduced pressure to give a syrup, which was subjected to column chromatography (silica gel, 50 g), first eluting with $CHCl_3$ (150 mL); 5% $Et_2O$/$CHCl_3$ eluted 34. Evaporation of solvent under reduced pressure gave 34 as a syrup (0.39 g; 0.31 g = 100%) which contained $CHCl_3$; TLC (silica gel, ca. 10% $Et_2O$/PhH): $R_f$ 0.7. Attempts to crystallize the product from $Et_2O$/heptane or $Et_2O$ failed. Dried at 65° C., 0.1 torr, the compound remained a syrup and then occluded $Et_2O$.

Anal. Calcd for $C_{25}H_{22}O_5$ + 0.2 $(C_2H_5)_2O$ [MW 417.28]: C, 74.26; H, 5.80. Found: C, 74.29 & 74.25; H, 5.89 & 5.92.

EXAMPLE 25

5-[2-[8-(1-Hydroxy)-2-phenylethyl]dibenzofuranyl]-5-oxopentanoic Acid (36). A solution of 34 (0.29 g, ca. 0.72 mmol) in MeOH (5 mL) and aqueous NaOH (1 mL, 1 M) was stirred at ambient temperatures for 2 h to give a mixture, which was then boiled for 1 h. Evaporation of most of the solvent in a stream of $N_2$ gave a nearly colorless paste A (compound 35). An aliquot was treated with $H_2O$ (2 mL), acidified with HCl (1.4 M), and extracted with $CHCl_3$ (3×1.5 mL). The extracts were dried ($MgSO_4$), and the solvent was evaporated under reduced pressure to give 36 (20 mg) as a syrup, which was dried at 65° C., 0.1 torr, 24 h, to give a froth.

Anal. Calcd for $C_{25}H_{22}O_5$ + 0.08 $CHCl_3$ [MW 412.01]: C, 73.11; H, 5.40. Found: C, 73.06 & 73.01; H, 5.64 & 5.66.

EXAMPLE 26

5-[2-[8-(1-Hydroxy)-2-phenylethyl]dibenzofuranyl]-5-hydroxypentanoic acid (45) and Its Lactone 44. The paste A in Example 25, containing ca. 0.67 mmol of the sodium salt 35, was treated with $H_2O$ (5 mL), warmed to effect solution, cooled, and then treated with $NaBH_4$ (25.4 mg) dissolved in $H_2O$ (0.5 mL) while stirring. After 15 min the entire material had formed a gelatenous ball around the magnetic stirring bar. After heating at ca. 60° C. for 70 min, a solution was obtained, which was treated with acetone (0.5 mL) and left to cool. Ice and HCl (1.4 N, 1.3 mL) were added to pH ~2, the mixture was twice extracted with $CHCl_3$ (ca. 40 mL, total), and the extracts were washed with ice-$H_2O$, dried ($MgSO_4$), and evaporated under reduced pressure to give a froth (0.25 g, 93%), which failed to crystallize from $Et_2O$ and consisted of ca. 1:1 44:45 ($^1$H and $^{13}$C NMR spectral analysis); TLC (silica gel, ca. 15% MeOH/$CHCl_3$): $R_f$ 0.9 and 0.4, respectively.

EXAMPLE 27

Sodium 5-[2-[8-(1-Hydroxy)-2-phenylethyl]dibenzofuranyl]-5-hydroxypentanoate (40). A solution of the mixture of 44 and 45 (0.25 g) in MeOH (7 mL) was clarified by filtration, then stirred with aqueous NaOH (1.4 mL, 0.71 M, ca. 1.6 equiv) for 2 h, concentrated under reduced pressure to ca. 1 mL, diluted with $H_2O$ (2 mL), and left to stand overnight. The solution was then percolated through DIAION HP-20 resin (ca. 35 mL of the beads) eluting with $H_2O$ and 5, 10, and 25% MeOH/$H_2O$ (30 mL each); 50% MeOH/$H_2O$ (100 mL) eluted a fraction I of 40 (0.12 g); MeOH (40 mL) eluted a fraction II of 40 (0.10 g). After the solvents had been evaporated under reduced pressure, fraction I was a colorless, turbid syrup while fraction II was a pale yellowish, clear syrup. $^1$H NMR ($D_2O$) spectra and TLC and HPLC retention times of fractions I and II were the same. HPLC: $R_t$ = 10.98 min, Spherisorb C-18 (10 μm) 4.6×300 mm, 80:20 0.01 M Fisher phosphate (pH 6.86) buffer:$CH_3CN$, flowrate 2 mL/min, UV detector (254 nm).

Each fraction was dissolved in $H_2O$ (5 mL) and subjected to freeze-drying to give a voluminous amorphous solid. During subsequent transfer, each collapsed to a sticky material that was dried at 65° C., 0.1 torr, overnight.

Anal. 40-I: Calcd for $C_{25}H_{23}O_5Na + 1.05\ H_2O$ [MW 445.37]: C, 67.42; H, 5.68. Found: C, 67.42 & 67.34; H, 5.69 & 5.75.

40-II: Calcd for $C_{25}H_{23}5Na + 1.3\ H_2O$ [MW 449.87]: C, 66.75; H, 5.74. Found: C, 66.89; H, 5.99.

EXAMPLE 28

N,N-Dimethyl-5-[2-[8-(1-tert-Butyldimethylsiloxy)-2-phenylethyl]dibenzofuranyl]-5-oxopentanamide (28). To a stirred solution of 3-bromopropionyl chloride (5.22 g, Aldrich, technical grade) in $CHCl_3$ (22 mL) at $-20°$ C. was added an ice-cold solution of $Me_2NH$ (2.34 g, 52 mmol, ca. 1.7 equiv) in $CHCl_3$ (18 mL, percolated through alumina and dried over 4 Å molecular sieves) during ca. 5 min. After the solution had warmed to ambient temperatures (45 min), it was extracted sequentially with ice-water (4×25 mL), sufficient aqueous NaOH (4.2 mL, 2.5 M) so that the aqueous layer was alkaline, and ice-water (2×25 mL), dried ($MgSO_4$), and the solvent was evaporated under reduced pressure. Distillation (55°–57° C., 0.15 torr) of the residue gave a clear, colorless liquid (3.14 g) that was a mixture of N,N-dimethyl 3-chloro- and 3-bromo-propanamides (ca. 1:3) according to GC/MS, $^1$H NMR spectroscopy, and elemental analysis.

Anal. Calcd for $C_5H_{10}NOCl_{0.26}Br_{0.74}$ C, 35.64; H, 5.98; N, 8.31; Halogen, 40.57. Found: C, 35.80 & 35.79; H, 5.99 & 6.01; N, 8.28 & 8.27; Halogen (for 74% Br & 26% Cl), 40.31.

A solution of the MMC adduct, prepared from the ketone 5 (0.89 g, 2 mmol) as in Example 19, was treated with the halopropanamide mixture (1.08 g) dissolved in dry DMF (1 mL) and then heated at 105° C. for 75 min, left to stand overnight, treated with another portion of halopropanamide (1.0 g, ca. 8 equiv, total), heated at 105° C. for 1 h, cooled, poured onto ice, and treated with HCl (1.4 M, 18 mL) to give a sticky solid which was filtered, rinsed with $H_2O$, and then dissolved in $CHCl_3$ (40 mL). The solution was dried ($MgSO_4$), and the solvent was evaporated under reduced pressure. The resulting syrup was fractionated on silica gel (50 g). PhH (200 mL), and 2, 5, and 20% $Et_2O$/PhH (100 mL each) eluted primarily 5 (0.75 g); $Et_2O$ eluted the amide 28 (0.08 g, ca. 50% based on nonrecovered 5); TLC (silica gel, $Et_2O$): $R_f$ ca. 0.4. A portion was dried at 65° C., 0.1 torr, 20 h, to give a tough, colorless syrup.

Anal. Calcd for $C_{33}H_{41}NO_4Si$ [MW 543.78]: C, 72.89; H, 7.60; N, 2.58. Found: C, 73.03; H, 7.68; N, 2.49.

EXAMPLE 29

N,N-Dimethyl-5-[2-[8-(1-hydroxy)-2-phenylethyl]-dibenzofuranyl]-5-oxopentanamide (37). Deblocking of 28 (0.29 g, 0.5 mmol) was carried out as in Example 11. The crude product was fractionated on silica gel (65 g): $CHCl_3$ (200 mL) and 2% MeOH/$CHCl_3$ (150 mL) eluted silicon compounds; 2 and 5% MeOH/$CHCl_3$ (50 and 160 mL, respectively) gave 37 (0.19 g, 80 %) as a syrup that contained ca. 1 mol $H_2O$ according to a $^1$H NMR spectrum; TLC (silica gel, $Et_2O$): $R_f$ 0.45. A portion was dried at 65° C., 0.1 torr, 2 d.

Anal. Calcd for $C_{27}H_{27}NO_4 + 0.29\ H_2O$ [MW 434.74]: C, 74.60; H, 6.40; N, 3.22. Found: C, 74.75 & 74.71; H, 6.40 & 6.43; N, 3.20.

EXAMPLE 30

N,N-Dimethyl-5-[2-[8-(1-hydroxy)-2-phenylethyl]-dibenzofuranyl]-5-hydroxypentanamide (41). The reduction of 37 (0.18 g, 0.42 mmol) and isolation of the product was carried out as in Example 18 to give 41 as a froth after drying at ambient temperatures, 0.1 torr (0.17 g, ca. 100%); TLC (silica gel, ca. 15% MeOH/$CHCl_3$): $R_f$ 0.6.

Anal. Calcd for $C_{27}H_{29}NO_4 + 1.2\ H_2O$ [MW 453.16]: C, 71.56; H, 6.99; N, 3.09. Found: C, 71.62 & 71.56; H, 6.79 & 6.B2; N, 3.04; Halogen, 0.0.

EXAMPLE 31

N-[5-[2-[8-(1-tert-Butyldimethylsiloxy)-2-phenylethyl]dibenzofuranyl]-5-oxopentanoyl]pyrrolidine (29). A solution of the ester 27 (0.29 g, 0.55 mmol) in pyrrolidine (3 mL, dried over 4 Å molecular sieves) containing a crystal of $NH_4Cl$ was refluxed under dry $N_2$ for 27 h. Most of the excess pyrrolidine was then boiled off. A $CHCl_3$ solution (30 mL) of the residue was washed with ice-water (25 mL) containing HCl (ca. 0.5 mL, 1.4 N) and ice-water, dried ($MgSO_4$), and evaporated under reduced pressure to give an orange syrup which was fractionated on silica gel (40 g). $CHCl_3$ eluted trace impurities; 1% MeOH/$CHCl_3$ eluted the amide 29, which was dried in vacuo to give a tough syrup (0.32 g, ca. 100%); TLC (silica gel, ca. 3% MeOH/$Et_2O$): $R_f$ 0.3. An analytical sample, dried at 65° C., 0.1 torr, for 17 h, was also a syrup. The compound ultimately crystallized and then had mp 90°–91° C.

Anal. Calcd for $C_{35}H_{43}NO_4Si$ [MW 569.82]: C, 73.77; H, 7.61; N, 2.46. Found: C, 73.50; H, 7.63; N, 2.41.

EXAMPLE 32

N-[5-[2-[8-(1-Hydroxy)-2-phenylethyl]dibenzofuranyl]-5-oxopentanoyl]pyrrolidine (38). Deblocking of the amide 29 (ca. 0.30 g, 0.5 mmol) and isolation of the product as in Example 11, gave a syrup, which was purified by chromatography on silica gel (40 g), first eluting with $CHCl_3$; 5% MeOH/$CHCl_3$ gave a syrup that solidified when treated with $Et_2O$. Filtration gave 38 as a colorless solid (0.18 g, ca. 75%), mp 137°–138° C., which was dried for 24 h, 65° C., 0.1 torr; TLC (silica gel, ca. 7% MeOH/$CHCl_3$): $R_f$ 0.5.

Anal. Calcd for $C_{29}H_{29}NO_4$ [MW 455.56]: C, 76.46; H, 6.42; N, 3.08. Found: C, 76.34; H, 6.46; N, 3.04.

EXAMPLE 33

N-[5-[2-[8-(1-Hydroxy)-2-phenylethyl]dibenzofuranyl]-5 hydroxypentanoyl]pyrrolidine (42). Compound 38 (ca. 0.15 g, 0.33 mmol) was reduced as in Example 18. The concentrated reaction mixture was treated with $CHCl_3$ (35 mL) and ice-water (25 mL). The organic layer was washed with ice-water (25 mL), dried ($MgSO_4$), and evaporated under reduced pressure to give 42 as a hard froth (0.16 g, 100%); TLC (silica gel, ca. 15% MeOH/$CHCl_3$): $R_f$ 0.4. On heating, the material begins to soften $>50°$ C. and gradually becomes a viscous syrup containing trapped gases. Analysis shows that some solvents remained trapped in the hard froth.

Anal. Calcd for $C_{29}H_{31}NO_4 + 0.17\ CHCl_3 + 0.20\ H_2O$ [MW 481.47]: C, 72.77; H, 6.61; N, 2.91; Cl, 3.76. Found: C, 72.82 & 72.77; H, 6.61 & 6.63; N, 2.89 & 2.89; Cl, 3.80.

EXAMPLE 34

N-[5-[2-[8-(1-tert-Butyldimethylsiloxy)-2-phenylethyl]dibenzofuranyl]-5-oxopentanoyl]morpholine (33). A stirred mixture of the ester 27 (0.98 g, 1.85 mmol), MeOH (20 mL), and aqueous NaOH (5.75 mL, 0.33 N) was heated near its boiling point for 2.5 h. When the clear solution was concentrated under reduced pressure; an oil separated and a voluminous froth formed when the volume was ca. 10 mL. The mixture was diluted with $CHCl_3$. Since an attempt to extract the solution with water gave an emulsion, saturated aqueous NaCl was added. When the emulsion had separated, the $CHCl_3$-layer was dried ($MgSO_4$) and evaporated under reduced pressure to give the sodium salt 31 as a thick syrup, which was dissolved in dry benzene (15 mL), and the solvent was again evaporated to dryness.

Conversion of 31 to the amide 33 via the acid chloride 32 was achieved as follows. A solution of 80% of the above syrup (31, 1.5 mmol) in dry benzene (16 mL) and pyridine (3 drops) was gradually added to a stirred solution of oxalyl chloride (0.25 mL, 2.9 mmol) in dry benzene (15 mL) under $N_2$ and cooled in an ice-bath. Since no evolution of gas was observed when ca. one-half of 31 had been added during 10 min, pyridine (3 drops) was added to the reaction mixture; a yellow solid separated at once and a gas was liberated. The remainder of 31 was added, alternating with pyridine (8 drops), followed by additional oxalyl chloride (0.13 mL; total, 4.5 mmol, 3 equiv), stirring was continued for 30 min, and morpholine (1.3 mL, 15 mmol, dried over 4 Å molecular sieves) was then added dropwise to the cold mixture during ca. 1 min. The mixture was left to stand overnight at ambient temperatures. Filtration and rinsing of the yellow, waxy solid with benzene (40 mL) gave a colorless filtrate, which was washed with ice-cold water (3×25 mL), dilute aqueous HCl (to give pH 4 after shaking), and water, dried ($MgSO_4$), and evaporated under reduced pressure to give a syrup of primarily 33. Column chromatography (silica gel, 90 g, $Et_2O$) gave trace amounts of impurities, followed by the amide, which was dissolved in PhH. Evaporation of volatiles gave 33 containing 1 mole of PhH ($^1$H-NMR spectral analysis, 0.84 g, ca. 90% overall from 27). A sample, dried at 65° C., 0.1 torr, for 7 h, was a hard glass; TLC (silica gel, $Et_2O$): $R_f$ ca. 0.2, (3% MeOH/PhH): $R_f$ ca. 0.4.

Anal. Calcd for $C_{35}H_{43}NO_5Si$ [MW 585.82]: C, 71.76; H, 7.40; N, 2.39. Found: C, 71.86; H, 7.44; N, 2.36.

EXAMPLE 35

N-[5-[2-[8-(1-Hydroxy)-2-phenylethyl]-dibenzofuranyl]-5 oxopentanoyl]morpholine (39). The procedure of Example 24 was used to deblock compound 33 (0.75 g, ca. 1.3 mmol). Evaporation of the dried $CHCl_3$ extract gave a clear syrup, which, upon addition of $Et_2O$ (ca. 40 mL), became opaque and gradually crystallized. The solid was rinsed with several portions of $Et_2O$, combined with similar material obtained in preliminary experiments (from ca. 0.37 g of 33), and purified by chromatography (silica gel, 90 g). $CHCl_3$-eluates (300 mL) were discarded; 4% MeOH/$CHCl_3$ gave in an early fraction impure 39 (65 mg, ca. 7%), followed by pure 39 (0.72 g, ca. 80%), mp 160.5°–161.5° C.; TLC (silica gel, 6% MeOH/$CHCl_3$): $R_f$ ca. 0.5.

Anal. Calcd for $C_{29}H_{29}NO_5$ + 0.14 $CHCl_3$ [MW 488.27]: C, 71.68; H, 6.02; N, 2.87. Found: C, 71.73 & 71.70; H, 6.16 & 6.18; N, 2.87.

EXAMPLE 36

N-[5-[2-[8-(1-Hydroxy)-2-phenylethyl]dibenzofuranyl]-5-hydroxypentanoyl]morpholine (43). The reduction (see Example 18) of 39 (0.40 g, 0.85 mmol) with $NaBH_4$ (35 mg, 0.9 mmol) was complete after 70 min at ca. 60° C. Decomposition of excess $NaBH_4$ with acetone and concentration under reduced pressure (to ca. 5 mL) gave a mixture, which was treated with $CHCl_3$ (40 mL) and washed with cold water (40 mL, then 2×30 mL). The organic layer was dried ($MgSO_4$) and evaporated under reduced pressure to give a L syrup, which was dissolved in $CH_2Cl_2$ (5 mL), and the solvent was again evaporated. This process was repeated to give 43 as a voluminous solid froth (0.40 g, 100%) after drying for 22 h, 0.1 torr; TLC (silica gel, 10% MeOH/$CHCl_3$): $R_f$ ca. 0.5.

Anal. Calcd for $C_{29}H_{31}NO_5$ + 0.03 $CH_2Cl_2$ + 0.45 $H_2O$ [MW 483.87]: C, 71.99; H, 6.66; N, 2.89. Found: C, 72.05 & 71.98; H, 6.70 & 6.73; N, 2.90.

EXAMPLE 37

Methyl 6-[2-[8-(1-tert-Butyldimethylsiloxy-2 phenylethyl]dibenzofuranyl]-6-oxohexanoate (46). A cooled solution of the MMC adduct, prepared from 5 (3.1 g, 7 mmol) as in Example 19, was treated with methyl 4-bromobutyrate (5.4 g, 30 mmol), heated for 16 h at 50° C. and 6 h at 85°–90° C., and then left overnight at ambient temperatures. No evolution of $CO_2$ was observed during the alkylation. The solution was poured into water + ice (ca. 200 g) and treated with sufficient aqueous HCl (1.45 N, 92 mL) to give pH 4 after extraction with $Et_2O$ (125 mL). The aqueous layer was again extracted with $Et_2O$ (50 mL), and the combined $Et_2O$ solutions were washed with ice + $H_2O$, dried ($MgSO_4$), and evaporated under reduced pressure to give a thick, orange syrup, which was fractionated by column chromatography (silica gel, 275 g, PhH). Early fractions contained the ethyl ketone 47 (0.62 g, 19%, colorless syrup); TLC (silica gel, PhH): $R_f$ 0.75. Middle fractions gave mixtures of 5 and methyl 4-bromobutyrate (2.47 g, ca. 1:1.5 w:w); late fractions gave 46 (1.62 g, 43%) as a pale yellow, thick syrup; TLC (silica gel, PhH): $R_f$ ca. 0.2. Samples of 47 and 46 were dried at 80° C., 0.1 torr, 5 h. Compound 46 later crystallized from heptane as a colorless solid, mp 69°–71° C.

Anal. (46) Calcd for $C_{33}H_{40}O_5Si$ [MW 544.77]: C, 72.76; H, 7.40. Found: C, 72.91; H, 7.44.

Anal. (47) Calcd for $C_{29}H_{34}O_3Si$ [MW 458.68]: C, 75.94; H, 7.47. Found: C, 75.95; H, 7.52.

Methyl 4-bromobutyrate was prepared by adding 4-bromobutyryl chloride (3.5 mL, 30 mmol) dropwise during 10 min to a cold solution of anhydrous MeOH (5 mL) in PhH (dry, 10 mL). The solution was left for ca. 1 h at ambient temperatures, diluted with PhH (to 50 mL), washed with ice + $H_2O$ (4×25 mL) until the washings were no longer acidic, dried ($MgSO_4$), and evaporated under reduced pressure to give a colorless liquid (6.2 g) that contained ca. ⅓ mol PhH per mol of the ester according to a $^1$H NMR spectrum.

EXAMPLE 38

N-[6-[2-[8-(1-tert Butyldimethylsiloxy-2-phenylethyl]dibenzofuranyl]-6-oxohexanoyl]pyrrolidine (48). Pyrrolidine (dried over 4 Å molecular sieves) was distilled prior to use (bp 86° C.). A solution of 46 (0.80 g, 1.47 mmol) in pyrrolidine (3.8 mL), protected against moisture with Drierite, was heated at 85° C. for 24 h and then evaporated with a stream of $N_2$ to give a thick, deep red syrup that was dissolved in $CHCl_3$ (50 mL). The solution was extracted with ice + $H_2O$ (30 mL) containing sufficient HCl (ca. 1.2 mL, 1.45 N) to give pH 5-6 after shaking. The nonemulsified $CHCl_3$ layer was separated and the aqueous layer and the emulsion inter-phase were again extracted with $CHCl_3$. The combined organic solutions were washed with ice + $H_2O$ containing some HCl, then with ice + $H_2O$ (the aqueous and emulsion layers each time being re-extracted with $CHCl_3$), and finally with saturated aqueous NaCl (25 mL) containing sufficient NaOH to give pH 8 after shaking. The combined $CHCl_3$-solutions were dried ($MgSO_4$) and evaporated under reduced pressure to give a residue which was fractionated by column chromatography (80 g silica gel, 2% $MeOH/CHCl_3$). The product 48 crystallized from heptane as an off-white solid (0.65 g, 77%), mp 101°-103° C.; TLC (silica gel, $Et_2O$): $R_f$ ca. 0.3.

Anal. Calcd for $C_{36}H_{45}NO_4Si$ [MW 583.85]: C, 74.06; H, 7.77; N, 2.40. Found: C, 74.00; H, 7.78; N, 2.48.

Further elution with 1% $AcOH/CHCl_3$ (100 mL) gave the acid 49 (0.06 g, 8%), which crystallized from $Et_2O$ and then had mp 132°-133.5° C.

Anal. Calcd for $C_{32}H_{38}O_5Si$ [MW 530.74]: C, 72.42; H, 7.22. Found: C, 72.27; H, 7.28.

EXAMPLE 39

N-[6-[2-[8-(1-Hydroxy)-2-phenylethyl]dibenzofuranyl]-6-oxohexanoyl]pyrrolidine (50). Deblocking of 48 (0.60 g, 1.03 mmol) was effected as in Example 11. The mixture, obtained when ice + $H_2O$ (ca. 40 g) were added, was extracted with $CHCl_3$ (50 mL, then 4×15 mL). The combined extracts were dried ($MgSO_4$) and evaporated under reduced pressure. When the resulting gum was stirred with $Et_2O$ (3×5 mL), it solidified. Additional solid, which precipitated from the $Et_2O$, was filtered. Evaporation of $Et_2O$ and drying at 0.1 torr gave a third crop of solid. [This procedure permits removal of all Si-containing compounds which are in part trapped by the gum.]The combined solids were purified by column chromatography (silica gel, 75 g), first eluting with $CHCl_3$ (150 mL); 5% $MeOH/CHCl_3$ (100 mL) gave a syrup that dissolved in $Et_2O$ (ca. 5 mL). On seeding, 50 precipitated as an off-white solid (0.48 g, ca. 100%); mp 128°-129.5° C.; TLC (silica gel, 10% $MeOH/CHCl_3$): $R_f$ ca. 0.6.

Anal. Calcd for $C_{30}H_{31}NO_4$ [MW 469.59]: C, 76.73; H, 6.65; N, 2.98. Found: C, 76.55; H, 6.68; N, 3.00.

EXAMPLE 40

N-[6-[2-8-(1-Hydroxy)-2-phenylethyl]dibenzofuranyl]-6-hydroxyhexanoyl]pyrrolidine (51). The reduction of 50 (0.41 g, 0.85 mmol), which was complete after 5 h, and the isolation of 51 were carried out as in Example 36. The dried product was a voluminous froth (0.40 g, 97%); TLC (silica gel, 10% $MeOH/CHCl_3$): $R_f$ ca. 0.4.

Anal. Calcd for $C_{30}H_{33}NO_4$ [471.60]: C, 76.41; H, 7.05; N, 2.97. Found: C, 76.18; H, 7.12; N, 2.94. Calcd for $C_{30}H_{33}NO_4$ + 0.07 $H_2O$ [472.86]: C, 76.20; H, 7.06; N, 2.96.

ASSAYS FOR BIOLOGICAL ACTIVITY ($LTB_4$)

Each compound was tested in two in vitro models of $LTB_4$ induced cell function. The cellular responses measured are presumed to be mediated via specific interactions of $LTB_4$ with cellular receptors. The results are shown in Table III.

The cellular responses studied include 1) $LTB_4$-induced degranulation (release of myeloperoxidase) from purified human neutrophils and 2) $LTB_4$-induced adhesion of human neutrophils to latex beads. Each putative antagonist was tested at 30 uM for its effect on each response. Selected compounds were tested in a concentration-response fashion.

(1) Neutrophil Degranulation Assay

Neutrophils are isolated from human venous blood via a twostep sedimentation procedure, and contaminating erythrocytes are selectively lysed. The neutrophils were preincubated in 0.25% Hanks buffer containing bovine serum albumin (BSA) with 5 ug Cytochalasin B/ml cells for 5 minutes at 37° C. Neutrophils ($4\times10^6$) are added to stimuli ($LTB_4$ or buffer control) in the presence and absence of antagonist in Krebs-Ringer buffer to a final volume of 1.0 ml, and incubated at 37° C. for appropriate periods of time. At the end of the reaction period the neutrophils are pelleted by centrifugation at 3000 rpm for 5 minutes at 4° C.

Aliquots (0.2 ml) of the supernatants are added to polystyrene tubes to which are added the following: 0.6 ml )>25% Hanks BSA, 0.5 ml MPO buffer (0.2 M $NaPO_4$, pH 6.2) and to start the color reaction 0.2 ml of a 1:1 v/v 0.05% $H_2O_2$:1.25 mg/ml dimethoxybenzidine (DMB). The reaction is allowed to run at room temperature for 15 minutes and is stopped by the addition of 0.05 ml 2% sodium azide. The developed color is quantitated in a spectrophotometer at 460 nm. The amount of myeloperoxidase (MPO) released by $LTB_4$ stimulation can thus be determined. In order to determine the total amount of MPO in the cells an unstimulated control tube of neutrophils is lysed using 0.01 ml 10% Triton TX and the total MPO is determined via the color reaction and spectrophotometer reading. The activity of a given concentration of $LTB_4$ is expressed as the percentage of the total MPO released. The activity of antagonists at a given concentration is expressed as a percentage of inhibiton of $LTB_4$-induced MPO release at a single concentration cf $LTB_4$.

(2) Neutrophil Latex Bead Adhesion

Latex bead suspension (0.6 ml; 10% aqueous suspension; particle diameter=1u) is pipeted into a 1.5 ml eppendorf centrifuge tube. The beads are pelleted by centrifugation, the supernatant is discarded and the beads are washed 2 times with 1 ml 0.9% saline. To the pelleted beads is added 0.5 ml saline and 0.5 ml 20 mg/ml human serum albumin (HSA) in Krebs-Ringer buffer. Allow bead-albumin mixture to sit at room temperature for 10 minutes, centrifuge for 1 minute and remove the supernatant, and wash albumin-coated beads 3 times with saline. Resuspend the beads in 1 ml of Krebs-Ringer.

Human neutrophils are prepared as described for the neutrophil degranulation assay and $10^7$ cells are added to 0.3 ml of Krebs-Ringer in the presence and absence of $LTB_4$ and putative antagonist and are incubated at 37° for an appropriate period of time.

The albumin-coated beads are then added in 0.05 ml to give a final bead concentration of 1% v/v, resulting in a bead to neutrophil ratio of 100:1. The tubes containing cells and beads are then placed in an agitating water bath at 37° C. and 120 oscillation per minute for 10 minutes. The reaction is stopped by adding an equal volume of 2.5% gluteraldehyde in saline. The reaction tubes are allowed to stand at room temperature for 30 minutes. The cells are then washed 3 times (with centrifugation at 1000 rpm for 5 minutes) with saline to remove the unadhered latex beads and resuspended in 0.3 ml saline.

Wet mounts are prepared and adherence is examined by light microscopy at 400x. Adherence is scored by counting five randomly placed fields of at least 50 neutrophils per field. The percentage of neutrophils that show adherent albumin-coated latex beads is determined by scoring as adherent all cells which exhibit one or more beads on their surface. Activity of the antagonists is expressed as the percent inhibition of $LTB_4$-induced adherence.

TABLE III

| Compound | LTB-Induced Neutrophil Degranulation | | LTB-Induced Neutrophil Bead Adhesion |
|---|---|---|---|
| | % Inhibition at 30 uM | $I_{50}$ | % Inhibition at 30 uM |
| 6 | | | |
| 11 | 35 | | 7 |
| 23 | 62 | | 10 |
| 25 | | | |
| 26 | | | |
| 40 | 38 | | 5 |
| 42 | 100 | 19 uM | 12 |
| 22 | 100 | | 1 |
| 12 | 100 | 13 uM | 14 |
| 41 | 57 | 9 uM | 2 |

It has thus been shown that there are provided compounds, compositions and methods which achieve the various objects of the invention and which are well adapted to meet the conditions of practical use.

As various possible embodiments might be made of the above invention, and as various changes might be made in the embodiments set forth above, it is to be understood that all matters herein described are to be interpreted as illustrative and not in a limiting sense.

What is claimed as new and desired to be protected by Letters Patent is set forth in the following claims.

We claim:

1. A compound having the formula:

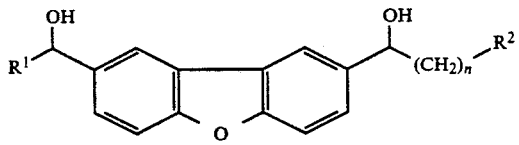

wherein
 (a) n is an integer from 1 to 5;
 (b) $R^1$ is selected from the group consisting of alkyl; phenyl, substituted phenyl substituted by Cl, Br, I, $-CF_3$, $-OCH_3$, alkyl, $-CN$, $-NH_2$, $-CONH_2$ or $NO_2$; $Ph(CH_2)_n$ wherein n is 1-5; Ph $(CH_2)_n$ wherein Ph is substituted by Cl, Br, I, $-CF_3$, $-OCH_3$, alkyl, $-CN$, $-NH_2$, $-CONH_2$ or $NO_2$; and
 (c) $R^2$ is selected from the group consisting of $CO_2R^3$ wherein $R^3$ is alkyl, aryl or aralkyl; alkanoate salt; $C(O)NR^4R^5$ wherein $R^4$ is H, alkyl or aryl and $R^5=R^4$ or is one of the other $R^4$ substituents, or $R^4$ and $R^5$ form a heterocyclic ring with the N as the sole heteroatom; tetrazole; sulfinic acid; sulfonic acid; and half esters of sulfur acids or sulfonamides derived therefrom.

2. A compound according to claim 1 wherein n is from 1 to 4.

3. A compound according to claim 2 wherein $R^1$ is benzyl.

4. A compound according to claim 3 wherein $R^2$ is $CO_2Na$, $C(O)N(CH_3)_2$,

or

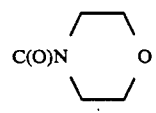

5. A compound according to claim 4 wherein n=1 and $R^2=C(O)N(CH_3)_2$.

6. A compound according to claim 4 wherein n=2 and $R^2$ is $CO_2Na$.

7. A compound according to claim 4 wherein n=2 and $R^2$ is $C(O)N(CH_3)_2$.

8. A compound according to claim 4 wherein n=2 and $R^2$ is

9. A compound according to claim 4 wherein n=3 and $R^2$ is $CO_2Na$.

10. A compound according to claim 4 wherein n=3 and $R^2$ is $C(O)N(CH_3)_2$.

11. A compound according to claim 4 wherein n=3 and $R^2$ is

12. A compound according to claim 4 wherein n=3 and $R^2=C(O)N$

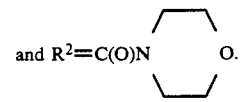

13. A compound according to claim 4 wherein n=4 and $R^2=C(O)N$

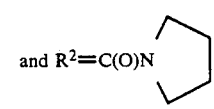

14. A pharmaceutical composition comprising a compound according to claim 1 in a pharmaceutical dosage from distributed in a pharmaceutical carrier.

15. A composition according to claim 14 wherein said dosage form is an oral dosage form selected from the group consisting of capsules, tablets, caplets, lozenges, liquids, elixirs and suspensions.

16. A composition according to claim 14 wherein said dosage form is a parenteral dosage form selected from the group consisting of injectable propylene glycol solutions and isotonic saline solutions.

17. A composition according to claim 14 wherein said dosage form is a topical dosage form selected from the group consisting of solutions, lotions, creams, ointments, powders and aerosol sprays.

18. A composition according to claim 14 wherein the compound of claim 1 is present in an amount effective to antagonize an $LTB_4$-mediated response in a human or animal patient.

19. A method of providing antagonism to an $LTB_4$-mediated response in a human or animal patient requiring such treatment comprising the administration to the patient of a pharmaceutical composition according to claim 18 from one to four times daily.

20. A method according to claim 19 wherein said pharmaceutical composition is administered orally.

21. A method according to claim 19 wherein said pharmaceutical composition is administered parenterally.

22. A method according to claim 19 wherein said pharmaceutical composition is administered topically.

23. A method according to claim 19 wherein the condition requiring $LTB_4$ medicated response is asthma, inflammatory and allergic disorders, immune system disorders, septic shock, renal disease, transplant rejection, psoriasis, arthritic, gout, cystic fibrosis, inflammatory bowel disease or pulmonary microembolization syndromes.

* * * * *